United States Patent
Ito

(10) Patent No.: US 9,879,215 B2
(45) Date of Patent: Jan. 30, 2018

(54) SUBJECT MOVING DEVICE

(71) Applicant: YAMAHA HATSUDOKI KABUSHIKI KAISHA, Shizuoka-ken (JP)

(72) Inventor: Saburo Ito, Shizuoka (JP)

(73) Assignee: YAMAHA HATSUDOKI KABUSHIKI KAISHA, Shizuoka-ken (JP)

( * ) Notice: Subject to any disclaimer, the term of this patent is extended or adjusted under 35 U.S.C. 154(b) by 106 days.

(21) Appl. No.: 15/102,103

(22) PCT Filed: Dec. 12, 2013

(86) PCT No.: PCT/JP2013/007332
§ 371 (c)(1),
(2) Date: Jun. 6, 2016

(87) PCT Pub. No.: WO2015/087371
PCT Pub. Date: Jun. 18, 2015

(65) Prior Publication Data
US 2016/0304821 A1 Oct. 20, 2016

(51) Int. Cl.
*C12M 1/32* (2006.01)
*C12M 1/00* (2006.01)
(Continued)

(52) U.S. Cl.
CPC ............ *C12M 33/04* (2013.01); *C12M 23/12* (2013.01); *C12M 23/50* (2013.01); *C12M 33/06* (2013.01);
(Continued)

(58) Field of Classification Search
None
See application file for complete search history.

(56) References Cited

U.S. PATENT DOCUMENTS 4,023,716 A 5/1977 Shapiro
5,275,951 A * 1/1994 Chow .................. B01L 3/0262
137/392
(Continued)

FOREIGN PATENT DOCUMENTS

CN 101865929 A 10/2010
CN 102753977 A 10/2012
(Continued)

OTHER PUBLICATIONS

International Search Report issued in PCT/JP2013/007332; dated Mar. 4, 2014.
(Continued)

*Primary Examiner* — P. Kathryn Wright
(74) *Attorney, Agent, or Firm* — Studebaker & Brackett PC

(57) ABSTRACT

A subject moving device includes: a base; a head section provided with vertically movable rods and moving along a prescribed movement path above the base; a first container section which stores a subject of movement; a second container section which receives the subject of movement; a tip stocking section which holds a plurality of tips in a state where the plurality of tips are attachable to the rods, the tips being attachable to and detachable from the rods and being configured to suction the subject of movement and discharge the suctioned subject of movement in accordance with vertical movements of the rods; a tip discarding section which collects the tips having finished the suction and the discharge of the subject of movement and having been detached from the rods; and a control section which controls the vertical movements of the rods and the movement operations of the head section.

9 Claims, 32 Drawing Sheets

(51) Int. Cl.
*G01N 35/10* (2006.01)
*C12M 1/26* (2006.01)
*C12M 1/36* (2006.01)

(52) U.S. Cl.
CPC ............ *C12M 41/48* (2013.01); *C12M 47/00* (2013.01); *G01N 35/1065* (2013.01); *G01N 2035/103* (2013.01)

(56) References Cited

U.S. PATENT DOCUMENTS

| | | |
|---|---|---|
| 2006/0051246 A1 | 3/2006 | Toi et al. |
| 2011/0143947 A1 | 6/2011 | Chamberlin et al. |
| 2014/0120192 A1 | 5/2014 | Nakayama et al. |
| 2014/0370589 A1 | 12/2014 | Ito |
| 2015/0072405 A1 | 3/2015 | Ito |

FOREIGN PATENT DOCUMENTS

| | | |
|---|---|---|
| EP | 2806020 A1 | 11/2014 |
| JP | H07-225235 A | 8/1995 |
| JP | H11-287812 A | 10/1999 |
| JP | 2001-074756 A | 3/2001 |
| JP | 2005-304303 A | 11/2005 |
| JP | 2006-078202 A | 3/2006 |
| JP | 2008-039747 A | 2/2008 |
| JP | 2008-175722 A | 7/2008 |
| JP | 2009-034013 A | 2/2009 |
| WO | 2011/081091 A1 | 7/2011 |
| WO | 2013/108293 A1 | 7/2012 |
| WO | 2013/108296 A1 | 7/2013 |

OTHER PUBLICATIONS

The First Office Action issued by the Chinese Patent Office dated Jan. 13, 2017, which corresponds to Chinese Patent Application No. 201380081553.8 and is related to U.S. Appl. No. 15/102,103; with English language summary.

The extended European search report issued by the European Patent Office dated Nov. 8, 2016, which corresponds to European Patent Application No. 13899024.7-1405 and is related to U.S. Appl. No. 15/102,103.

Y. Zheng, et al.; "Robotics for Biological and Medical Applications"; Robotics Report; Feb. 16, 2006; pp. 63-72; Chapter 6; National Science Foundation; USA.

Extended European Search Report (EESR) dated Apr. 11, 2017 from corresponding EP Appl No. 17000292.7, 10 pp.

An Office Action issued by U.S. Patent and Trademark Office dated Nov. 15, 2017, which corresponds to U.S. Appl. No. 15/435,435 and is related to U.S. Appl. No. 15/102,103.

\* cited by examiner

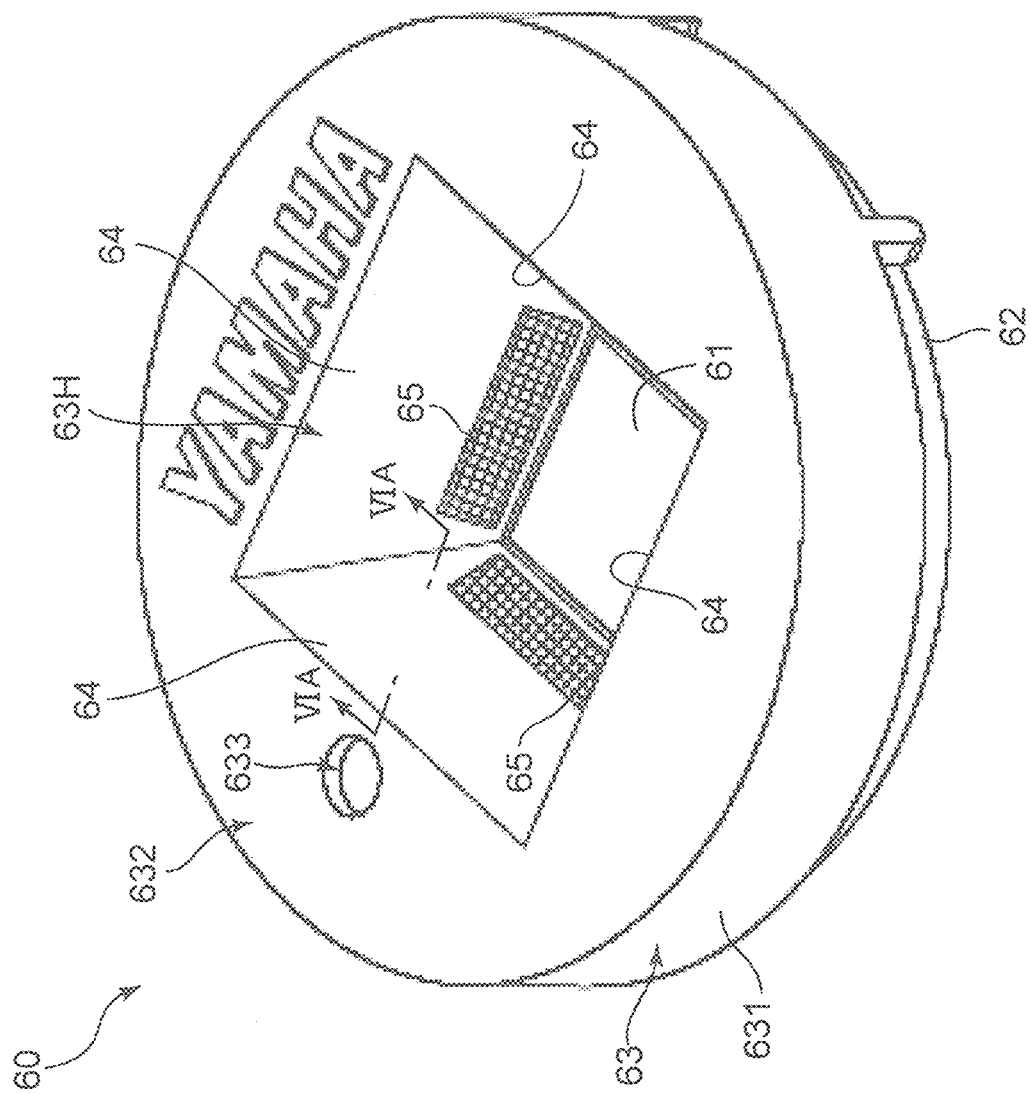

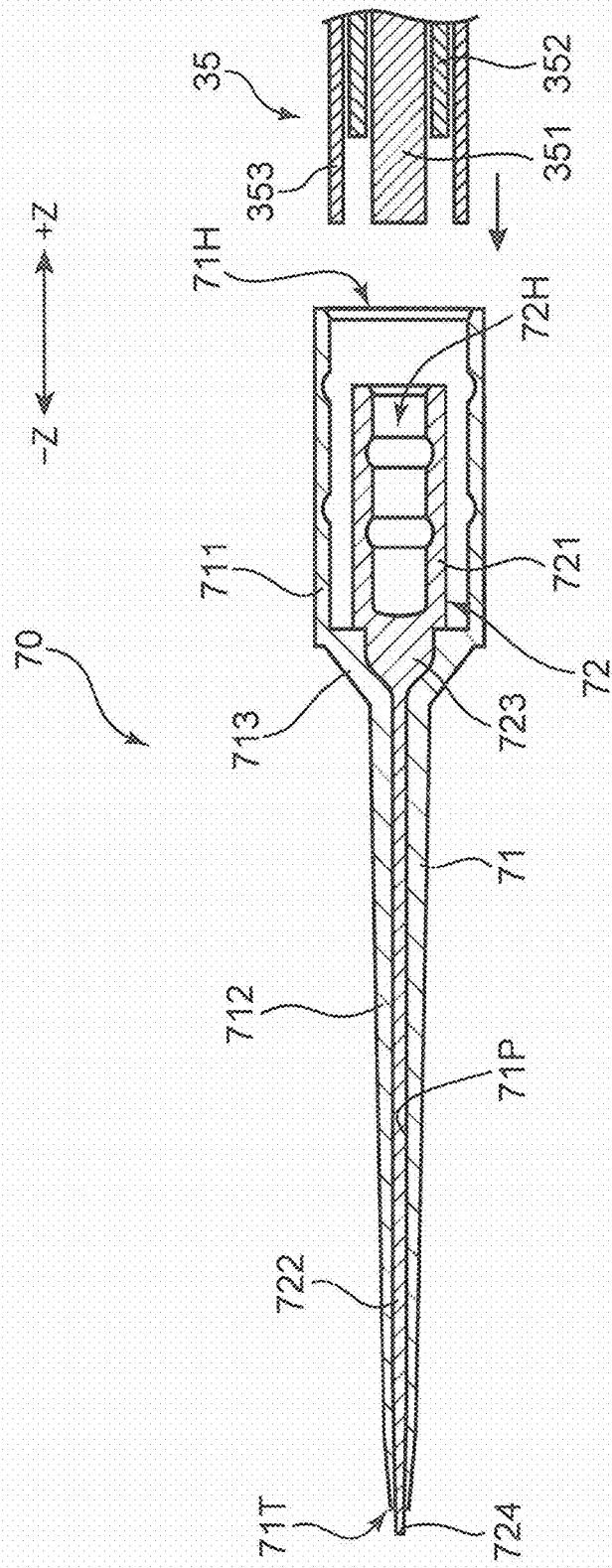

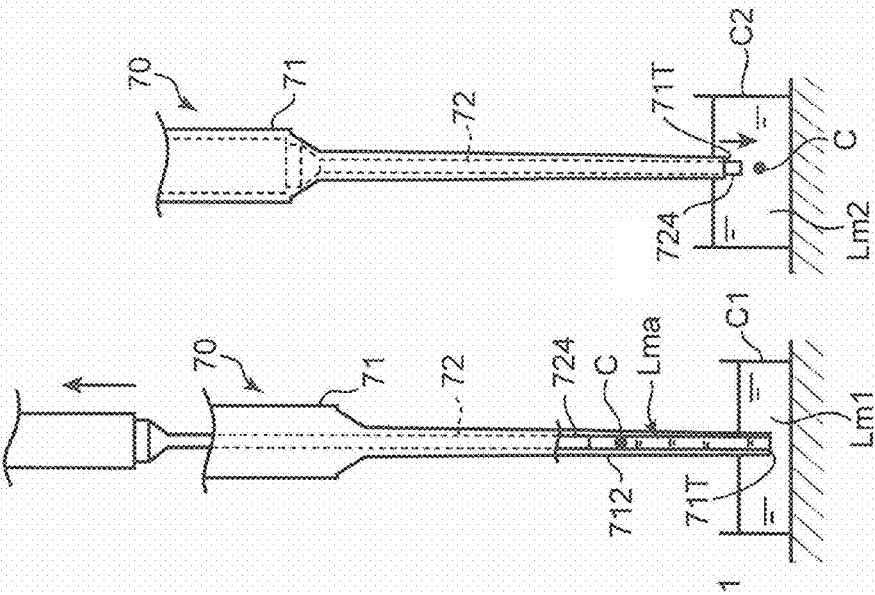

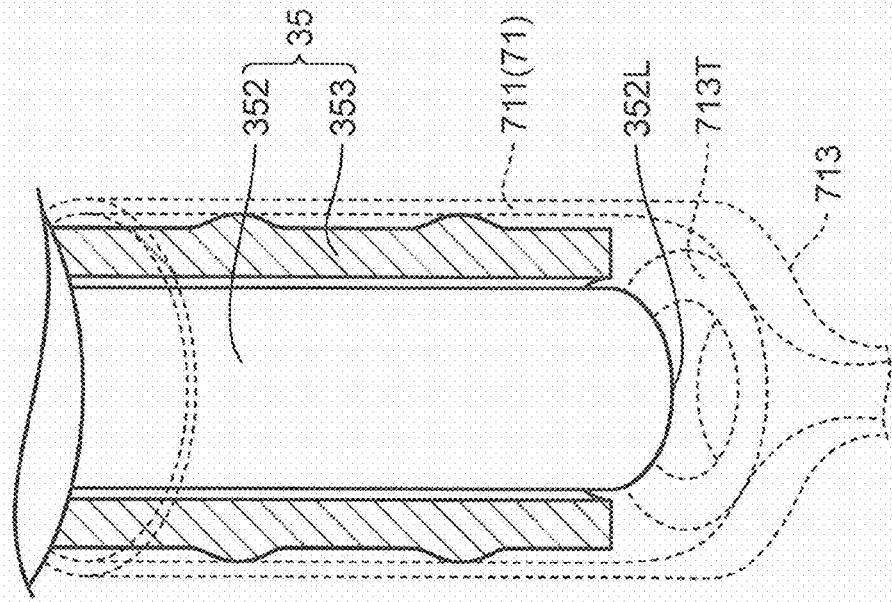
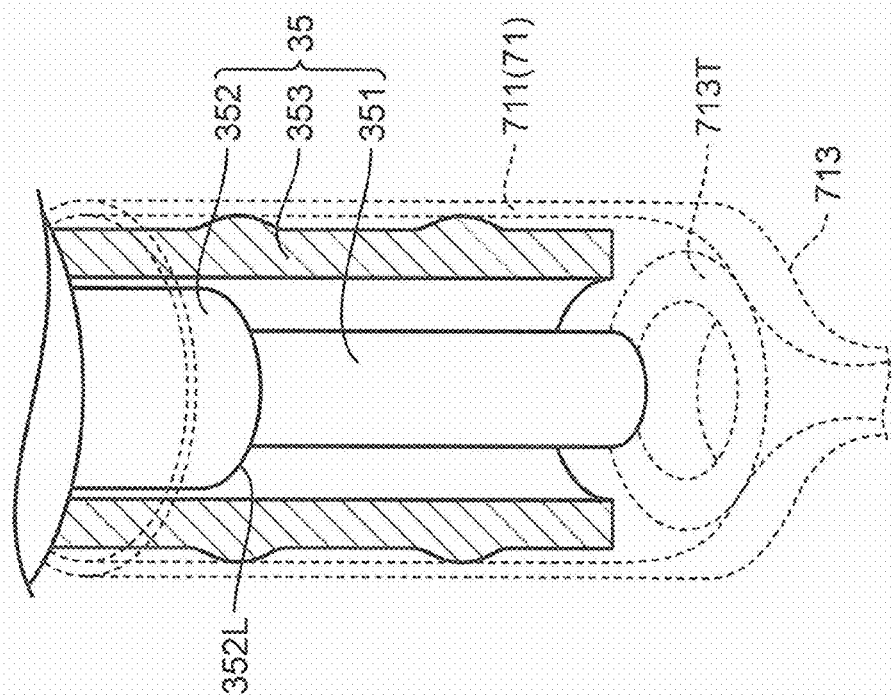

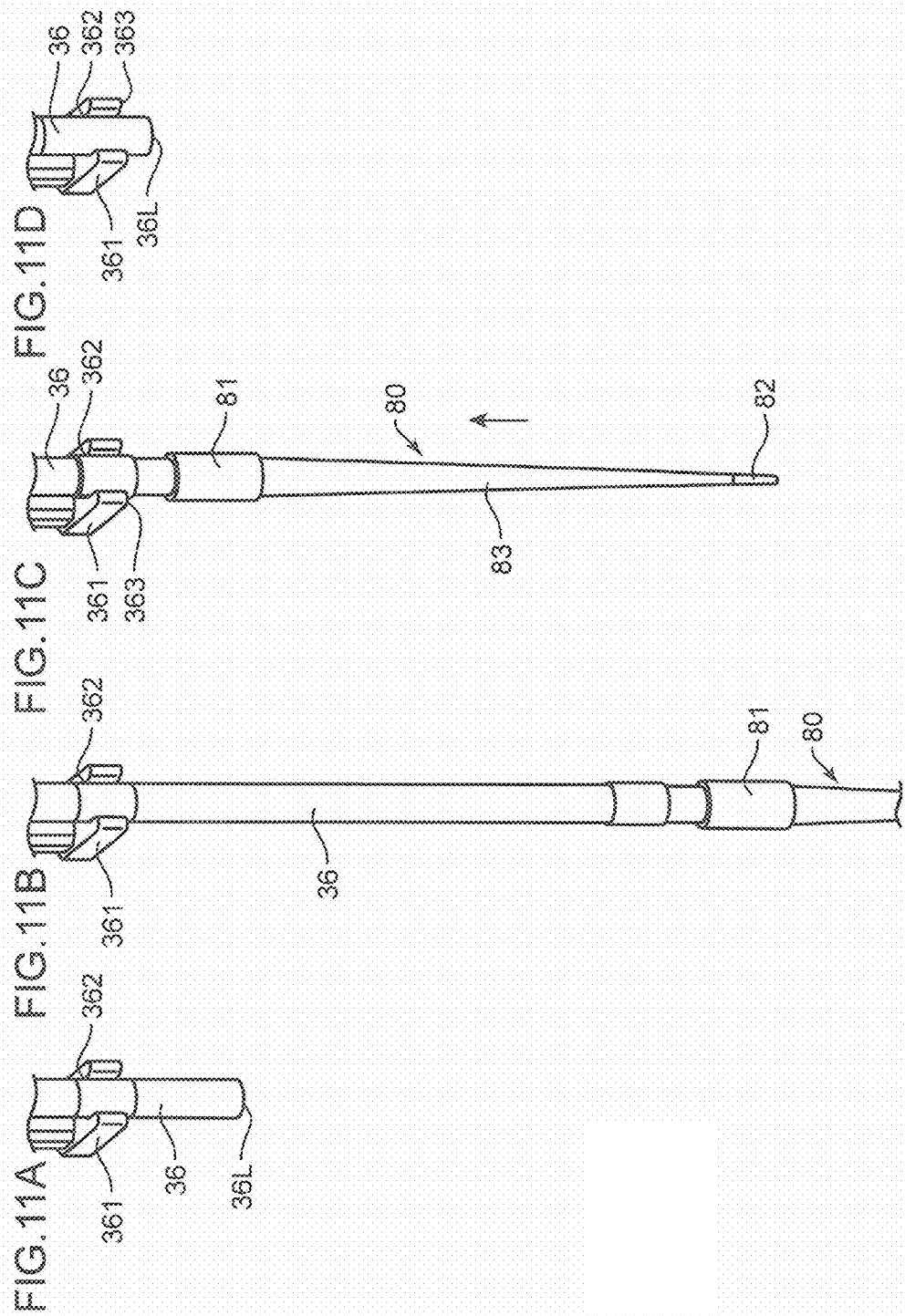

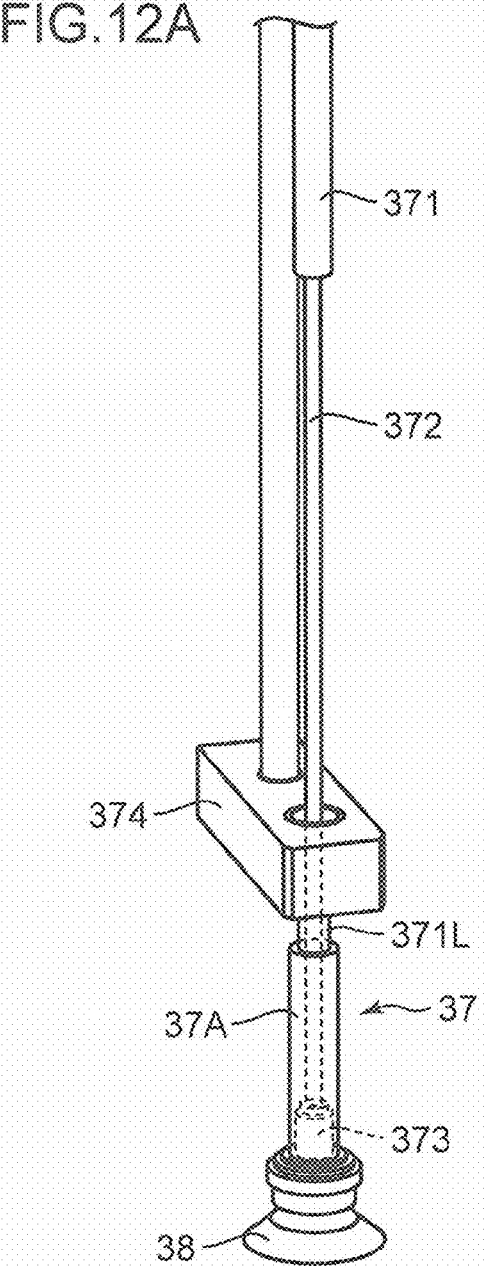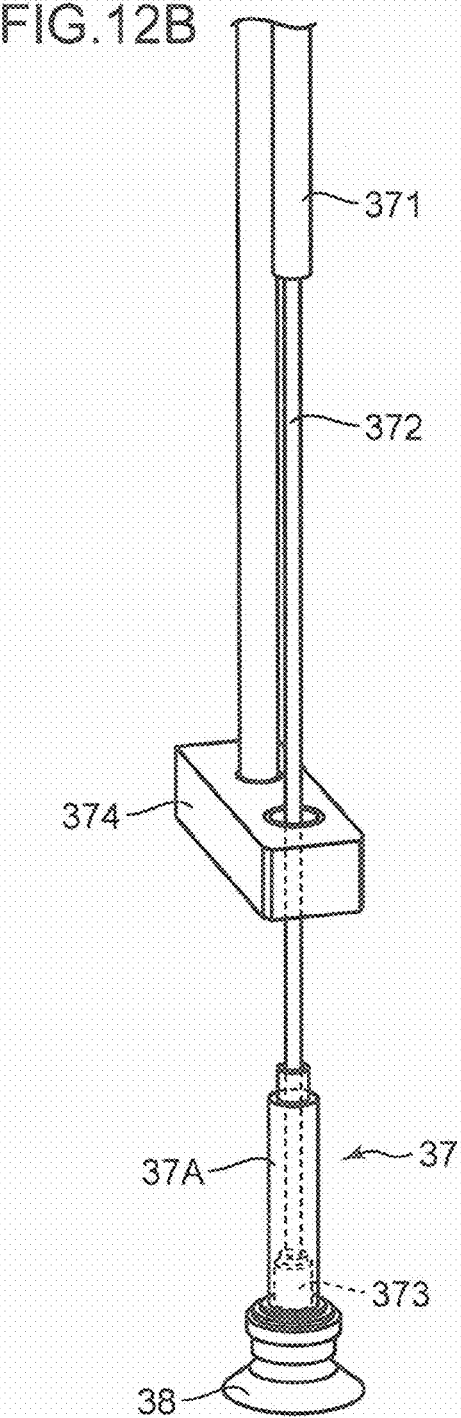

SUBJECT MOVING DEVICE

CROSS REFERENCE TO RELATED APPLICATIONS

This application claims benefit of priority to International Patent Application No. PCT/JP2013/007332 filed Dec. 12, 2013, the entire content of which is incorporated herein by reference.

TECHNICAL FIELD

The present disclosure relates to a moving device which moves a subject such as a cellular aggregate from one container to another container.

BACKGROUND

Moving devices which move a subject from one container to another container are required in various technical fields. An example of a moving device is a device including a first container that stores a large number of subjects of movement such as small parts, organic or inorganic crushed pieces or particles, and cells and a second container that receives the subjects of movement, wherein the device extracts some of the subjects of movement from the first container and moves the subjects of movement to the second container.

Japanese Unexamined Patent Publication No. 2009-34013 discloses a technique in which a cellular aggregate is assumed as a subject of movement and in which the cellular aggregate is suctioned from a dispensing well using a suction tip (a micropipette) and discharged to a cell petri dish. The cellular aggregate is held in a liquid and, during the suction, a distal end opening of the suction tip is immersed in the liquid. Therefore, in some cases, the suction tip may have to be discarded after each suction and discharge.

There are demands for highly automating a series of operations including suction and discharge described above in a movement operation of a cellular aggregate. However, as things stand, such a movement operation is either entirely performed manually or performed using a simple moving device only equipped with a mechanism for generating a suction force and a mechanism for moving a suction tip. Therefore, operational efficiency of the movement operation cannot be described as being favorable.

SUMMARY

An object of the present disclosure is to realize, in a moving device which moves a subject from one container to another container, the movement with good operational efficiency.

A subject moving device according to an aspect of the present disclosure includes: a base; a head section which is provided with vertically movable rods and which moves along a prescribed movement path above the base; a first container section which has an open upper surface and which stores a subject of movement; a second container section which has an open upper surface and which receives the subject of movement; a tip stocking section which holds a plurality of tips in a state where the plurality of tips are attachable to the rods, the tips being attachable to and detachable from the rods and being configured to suction the subject of movement and discharge the suctioned subject of movement in accordance with vertical movements of the rods; a tip discarding section which collects the tips having finished the suction and the discharge of the subject of movement and having been detached from the rods; and a control section which controls the vertical movements of the rods and the movement operations of the head section. The first container section, the second container section, the tip stocking section, and the tip discarding section are assembled to the base along a movement path of the head section.

Control performed by the control section includes the following which are sequentially performed: first control for moving the head section to above the tip stocking section and attaching the tips to the rods; second control for moving the head section to above the first container section and suctioning the subject of movement stored in the first container section into the tips; third control for moving the head section to above the second container section and discharging the subject of movement in the tips to the second container section; and fourth control for moving the head section to above the tip discarding section, and detaching the tips from the rods, and moreover discarding the tips to the tip discarding section.

The above and other objects, features, and advantages of the present disclosure will become apparent from a reading of the following detailed description when considered in connection with the accompanying drawings.

BRIEF DESCRIPTION OF DRAWINGS

FIG. 5 is a perspective view of a dish to which a liquid containing a cellular aggregate as a subject of movement is dispensed.

FIG. 8 is a sectional view of a cylinder tip.

FIGS. 9A to 9E are schematic views showing suction and discharge operations of a cellular aggregate by the cylinder tip.

FIGS. 10A and 10B are partially-cutaway perspective views for explaining an attaching/detaching operation of the cylinder tip to/from a rod provided in the head section.

FIGS. 11A to 11D are perspective views for explaining an attaching/detaching operation of a dispensing tip to/from a nozzle provided in the head section.

FIGS. 12A and 12B are perspective views of a suction disk head.

DETAILED DESCRIPTION

Hereinafter, an embodiment of a subject moving device according to the present disclosure will be described in detail with reference to the drawings. In the embodiment, a case will be described where a subject of movement is a biological cell and, in particular, a cellular aggregate. Moreover, the subject of movement is not limited to a cellular aggregate and may be a small electronic part or a small mechanical part, an organic or inorganic crushed piece or particle, a pellet, or the like.

Figure 1:
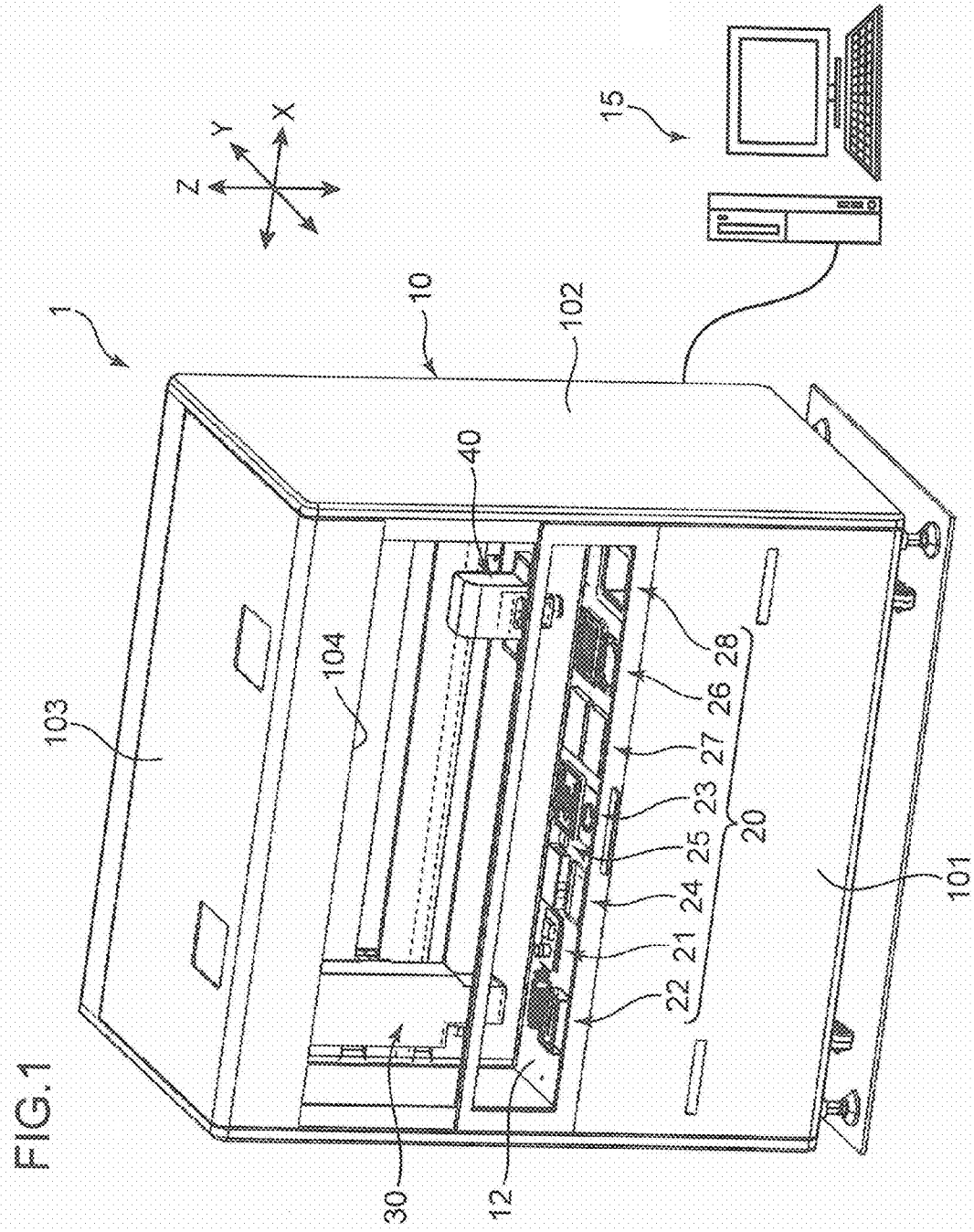
FIG. 1 is a perspective view showing an external appearance of a moving device according to an embodiment of the present disclosure.

FIG. 1 is a perspective view showing an external appearance of a moving device 1 of a cell according to an embodiment of the present disclosure. The moving device 1 includes a device main body 10 and a control section 15 constituted by a personal computer, a control board, or the like which controls operations of respective sections of the device main body 10. The device main body 10 is covered by a box-shaped outer cover or, more specifically, a front cover 101, a side cover 102, a top cover 103, and a rear cover not depicted in the drawing. An opening 104 is provided in an upper part of the front cover 101 and the interior of the device main body 10 is exposed through the opening 104. The control section 15 is connected to the device main body 10 so as to be capable of communication.

Figure 2:
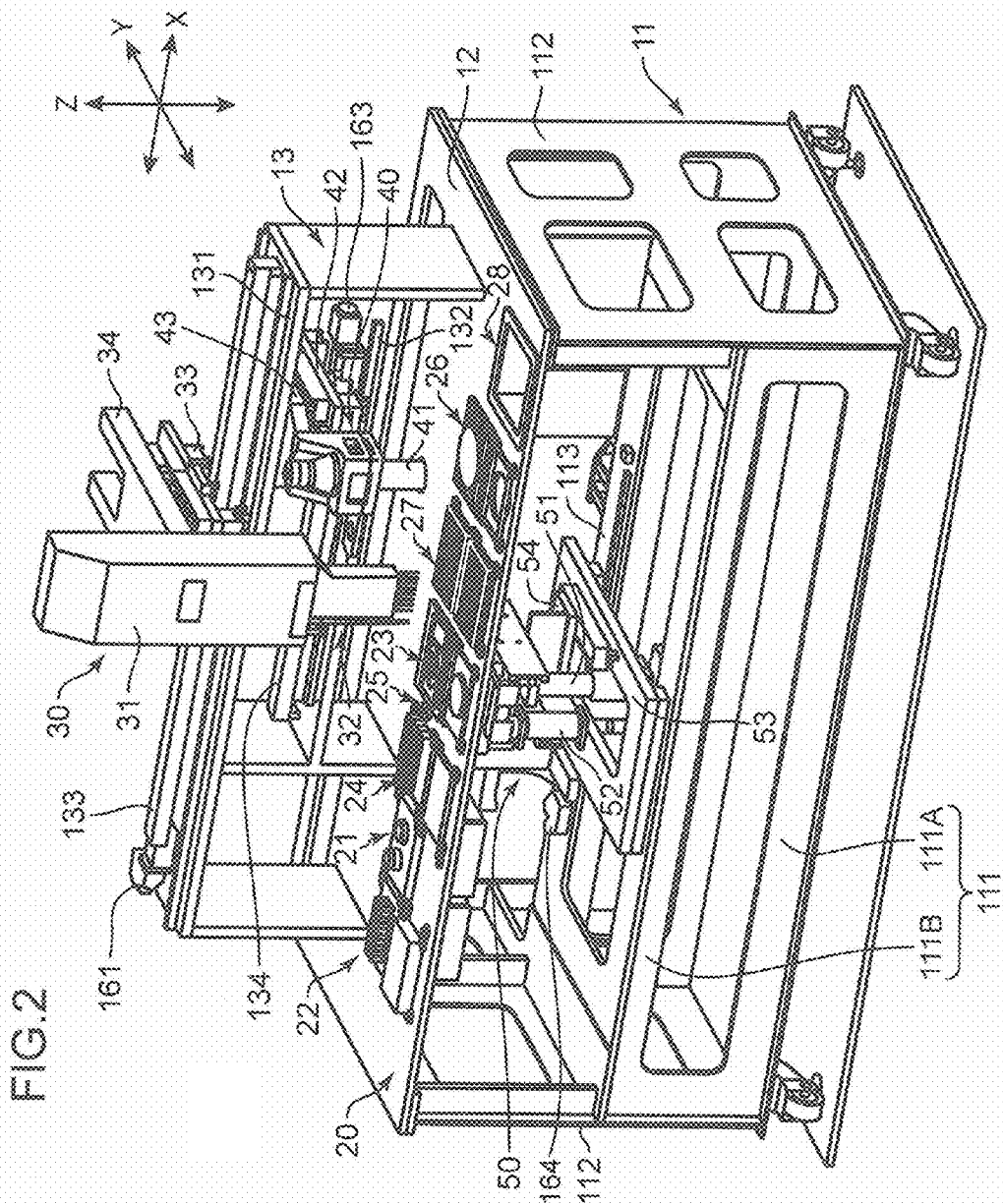
FIG. 2 is a perspective view of the moving device in a state where an outer cover has been removed.
Figure 3:
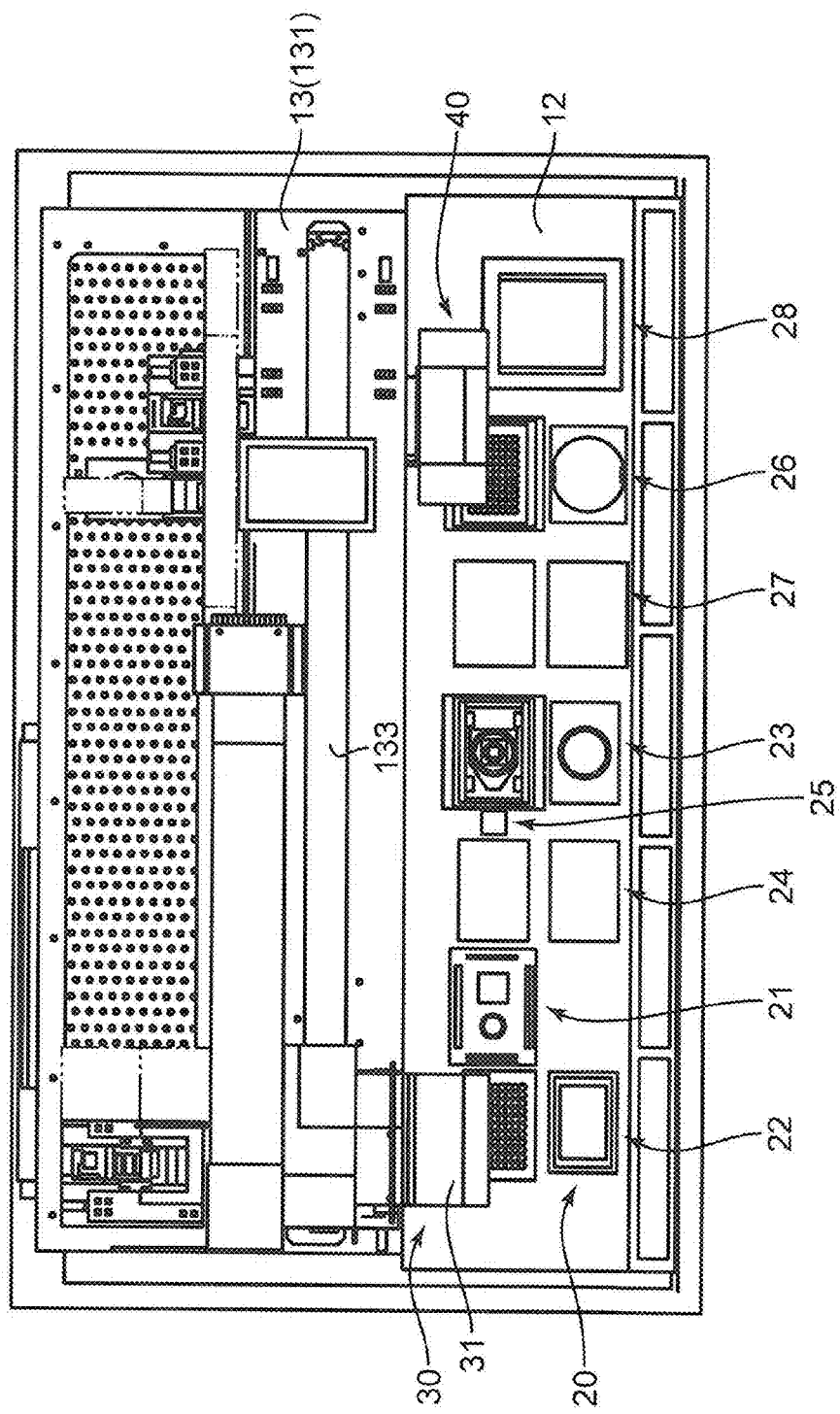
FIG. 3 is a plan view of the moving device as viewed from above.

FIG. 2 is a perspective view of the moving device 1 (the device main body 10) in a state where the outer cover has been removed, and FIG. 3 is a plan view of the moving device 1 as viewed from above. The moving device 1 includes a supporting frame 11, a base 12 which is supported by the supporting frame 11, a cell movement line 20 which is assembled to the base 12, a head unit 30 and a lighting unit 40 (a lighting section) which are arranged above the base 12, and an imaging unit 50 (a tip imaging device; a subject observing device) which is arranged below the base 12.

The supporting frame 11 includes a base frame 111 and a pair of side frames 112. The base frame 111 is a rectangular parallelepiped-shaped frame assembly which is elongated in an X direction and which includes a rectangular lower layer frame 111A and an upper layer frame 111B above the lower layer frame 111A. A guide rail 113 for moving the imaging unit 50 in the X direction is provided on an upper surface of the upper layer frame 111B. Casters are attached to four corners of a lower surface of the lower layer frame 111A. The side frames 112 are frames which respectively protrude upward (a Z direction) from both ends in the X direction of the base frame 111. Both ends in the X direction of the base 12 are respectively supported by upper end edges of the two side frames 112.

The base 12 is a rectangular flat plate which has prescribed rigidity, which is formed by a translucent material, and which has an approximately same size as the base frame 111 in an upper view. In the present embodiment, the base 12 is a glass plate. Forming the base 12 using a translucent material such as a glass plate has an advantage in that imaging of the respective sections of the cell movement line 20 arranged on an upper surface of the base 12 can be performed through the base 12 by the imaging unit 50 arranged below the base 12. Alternatively, a sheet metal plate having a glass window only in a portion necessary for the imaging may be used as the base 12.

A frame rack 13 is erected on the base 12. The frame rack 13 includes an upper frame 131 which is a flat plate extending in the X direction and a middle frame 132 which is also a flat plate extending in the X direction and which is arranged at an interval below the upper frame 131. An upper guide rail 133 for moving the head unit 30 in the X direction (along a prescribed movement path) is assembled to an upper surface of the upper frame 131. In addition, a middle guide rail 134 for moving the lighting unit 40 in the X direction is assembled to an upper surface of the middle frame 132.

The cell movement line 20 is constituted by aligning, in the X direction, elements necessary for performing a series of cell movement processes for extracting a desired cellular aggregate from a cell-containing liquid and moving the cellular aggregate to a prescribed container. The cell movement line 20 includes a subject stocking section 21 (a third container section) which stores a cell-containing liquid, a dispensing tip stocking section 22, a cell selecting section 23 (a first container section) to which the cell-containing liquid is dispensed and which is used to select a cellular aggregate, a tip stocking section 24, a tip imaging section 25, a cell transferring section 26 (a second container section) which receives a selected cellular aggregate, a black cover mounting section 27, and a tip discarding section 28. Details of the respective sections will be given later.

Figure 7:
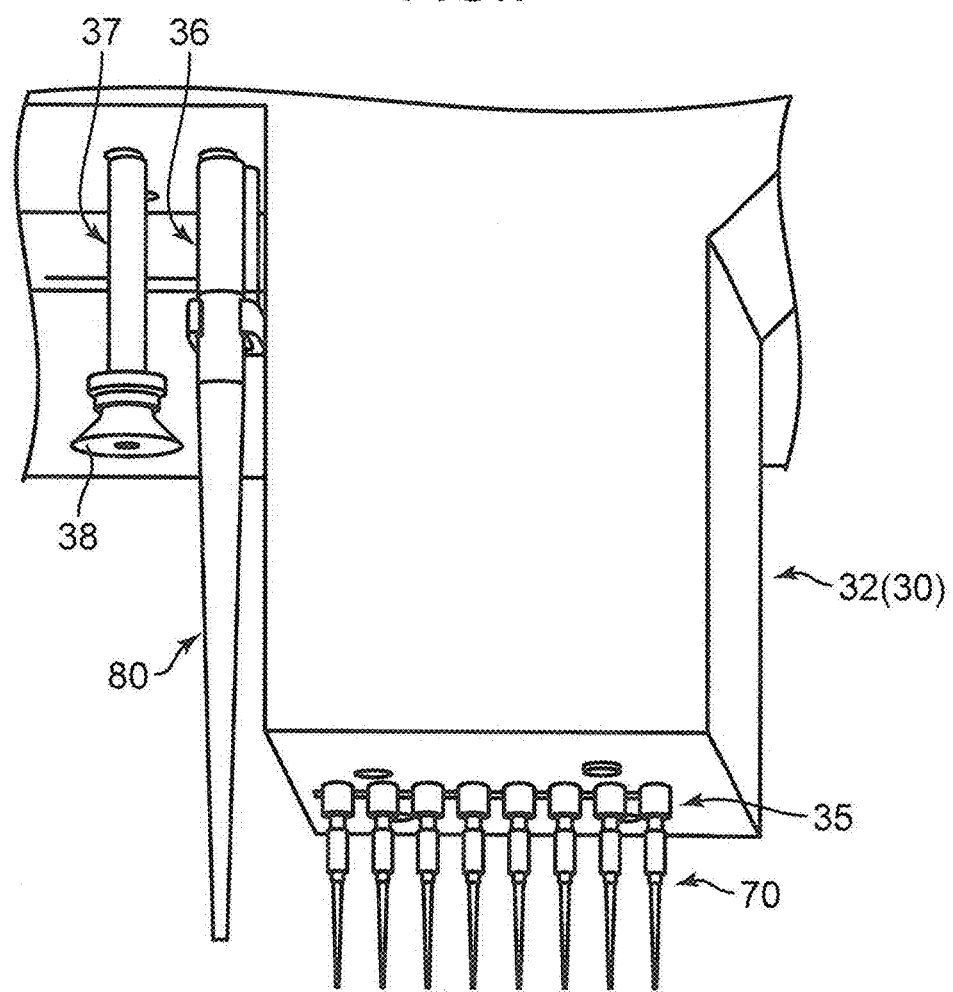
FIG. 7 is a perspective view of a head section.

The head unit 30 includes a unit main body 31, a head section 32, an X slider 33, and a Y slider 34. FIG. 7 is a perspective view of the head section 32. The head section 32 includes a plurality of rod sections 35 which are vertically movable, a first nozzle 36, and a second nozzle 37. The rod sections 35 include vertically movable rods 351 (refer to FIG. 8) and are provided so as to protrude on a lower end surface of a housing of the head section 32. In the present embodiment, an example is shown in which eight rod sections 35 are aligned in a single row in the X direction. The number of rod sections 35 is arbitrary and the rod sections 35 may be arranged in a matrix pattern in X-Y directions. The first nozzle 36 and the second nozzle 37 are assembled to the unit main body 31 so as to be vertically movable. Openings are provided at lower ends of the first nozzle 36 and the second nozzle 37, and piston mechanisms (to be described later) for generating a suction force and a discharge force at the openings are provided inside the first nozzle 36 and the second nozzle 37. A head driving device 162 (refer to FIG. 29) which includes a mechanism for vertically moving the rod sections 35, the first nozzle 36, and the second nozzle 37 and a mechanism for operating the rods 351 and the piston mechanisms is built into the unit main body 31.

The X slider 33 is assembled to the upper guide rail 133 which extends in the X direction. A head unit driving device 161 (a first driving mechanism) is annexed to the upper guide rail 133. Due to an operation of the head unit driving device 161, the X slider 33 moves in the X direction on the upper guide rail 133. The Y slider 34 supports the unit main body 31 at one end (a front end) in the Y direction. The Y slider 34 is assembled to a Y rail (not shown in FIG. 2) which is arranged on an upper surface of the X slider 33. Due to an operation of a driving device (not shown) which is annexed to the Y rail, the Y slider 34 and the unit main body 31 move in the Y direction. In other words, the head section 32 is freely movable in the X and Y directions due to movements of the unit main body 31 along the upper guide rail 133 and the Y rail. Therefore, the head section 32 is capable of moving along a prescribed movement path on the cell movement line 20 above the base 12.

The lighting unit 40 is movably arranged above the base 12 in order to exclusively illuminate the cell selecting section 23 and the cell transferring section 26 from above. The illumination is used as transmissive illumination when imaging of a cellular aggregate held by the cell selecting section 23 or the cell transferring section 26 is performed by the imaging unit 50. The lighting unit 40 includes an illuminator 41 (a light source) which emits illuminating light, an X slider 42, and a holder 43. The illuminator 41 includes a cylindrical housing extending in the Z direction, a halogen lamp as a light source and optical parts such as a collector lens, a ring slit, an aperture diaphragm, and a condenser lens, which are arranged in the housing. A tungsten lamp, a mercury lamp, a xenon lamp, a light-emitting diode (LED), or the like can be used instead of the halogen lamp.

The X slider 42 is assembled to the middle guide rail 134 which extends in the X direction. A lighting unit driving device 163 (a second driving mechanism) is annexed to the middle guide rail 134. Due to an operation of the lighting unit driving device 163, the X slider 42 moves in the X direction on the middle guide rail 134. The holder 43 holds the illuminator 41 and is assembled to the X slider 42 so as to be movable only by a short distance in the Y direction by a driving device (not shown). Therefore, the illuminator 41 is movable in the X and Y directions above the base 12. While the illuminator 41 is capable of moving between the cell selecting section 23 and the cell transferring section 26 in the X direction in the present embodiment, alternatively, the illuminator 41 may be configured so as to be movable over an entire length in the X direction of the cell movement line 20.

The imaging unit 50 is movably arranged below the base 12 in order to capture images of the cellular aggregate held by the cell selecting section 23 and the cell transferring section 26 from below the base 12. In addition, in the present embodiment, the imaging unit 50 is also used to observe an attachment state of a cylinder tip 70 (FIG. 4) to the rod section 35 by the tip imaging section 25. The imaging unit 50 includes a camera 51 (an imaging section), a vertical illuminator 52, an X slider 53, and a holder 54.

The camera 51 includes a CCD image sensor and an optical system which forms an optical image on a light-receiving surface of the CCD image sensor. The vertical illuminator 52 is a light source which is used when an imaging subject of the camera 51 is not a light-transmitting body and is arranged to the side of the camera 51. In the present embodiment, when capturing an image of the cellular aggregate, the camera 51 performs an imaging operation in a state where the illuminator 41 of the lighting unit 40 is turned on (transmissive illumination). On the other hand, when capturing an image of the tip by the tip imaging section 25, the camera 51 performs an imaging operation in a state where the vertical illuminator 52 is turned on (side illumination). Alternatively, the imaging unit 50 may be equipped with a dedicated lighting device for capturing images of the tip.

The X slider 53 is assembled to the guide rail 113 of the supporting frame 11 which extends in the X direction. An imaging unit driving device 164 is annexed to the guide rail 113. Due to an operation of the imaging unit driving device 164 (a third driving mechanism), the X slider 53 moves in the X direction on the guide rail 113. The holder 54 holds the camera 51 and the vertical illuminator 52 and is assembled to the X slider 53 so as to be movable only by a short distance in the Y direction by a driving device (not shown). Therefore, the camera 51 is movable in the X and Y directions below the base 12. In the present embodiment, the camera 51 is movable between the tip imaging section 25 and the cell transferring section 26 in the X direction. However, in other embodiments in which images of a tip are not captured, the camera 51 need only be movable at least between the cell selecting section 23 and the cell transferring section 26.

Figure 4:
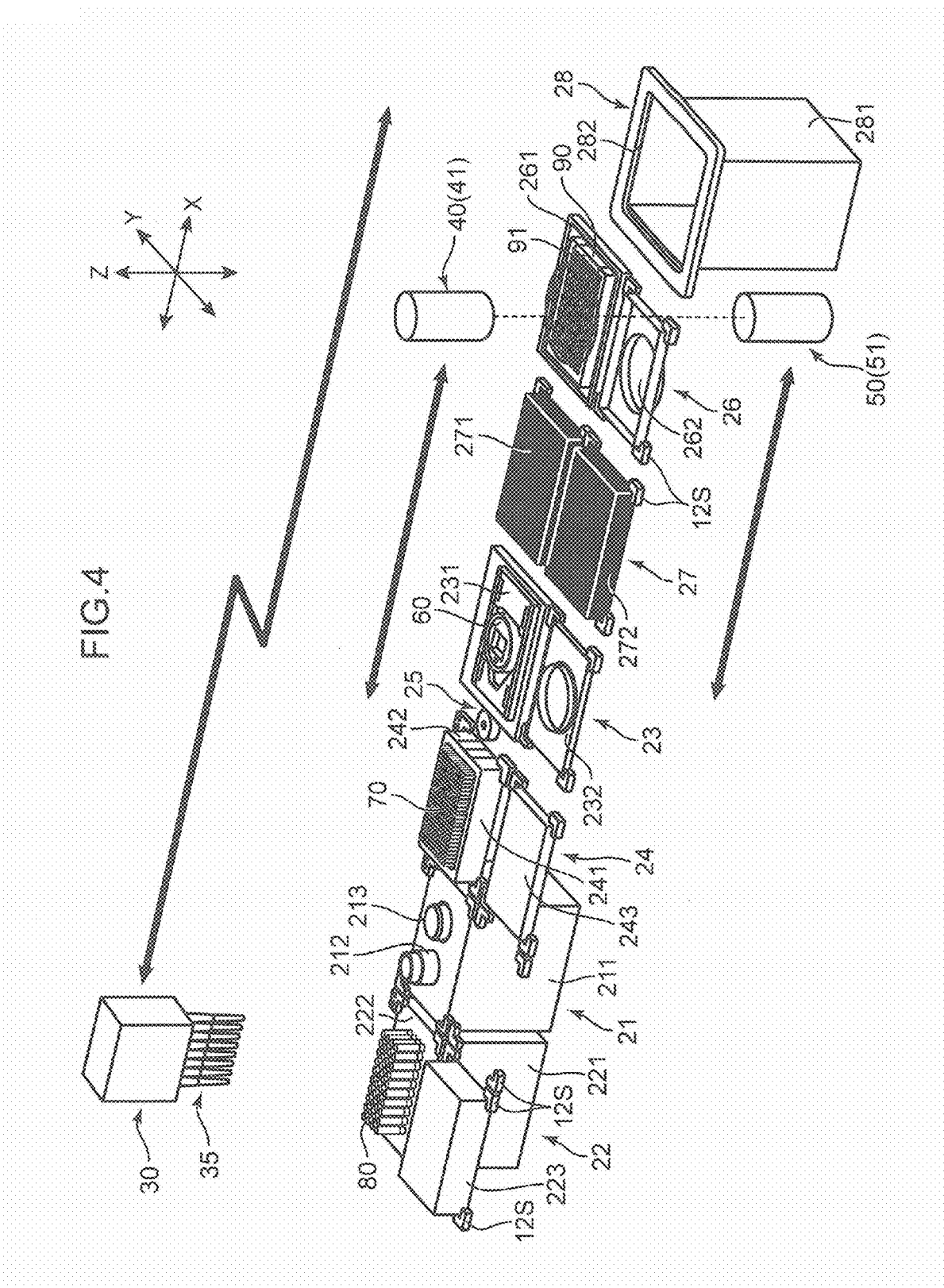
FIG. 4 is a perspective view showing components of a cell movement line in the moving device.

FIG. 4 is a perspective view which omits the base 12 and which extracts and shows components of the cell movement line 20. FIG. 4 also schematically shows arrangement positions of the head unit 30, the lighting unit 40, and the imaging unit 50 described above. The cell movement line 20 is constituted by sequentially aligning, from an upstream side in the X direction (a left end side in FIG. 4), the dispensing tip stocking section 22, the subject stocking section 21, the tip stocking section 24, the tip imaging section 25, the cell selecting section 23, the black cover mounting section 27, the cell transferring section 26, and the tip discarding section 28. Positions of the respective sections on the base 12 are determined by a positioning member 12S.

The subject stocking section 21 is a part which acts as an dispensation source and which stores a cell culture solution (liquid) in which a cellular aggregate (a subject of movement; a biological cell) is dispersed in a large amount. The subject stocking section 21 includes a box 211 arranged at a prescribed position on the base 12, a tube 212 (a third container section) held by the box 211, and a lid member 213 placed on the box 211. The box 211 holds the tube 212 in a state where an upper end of the tube 212 protrudes from the box 211. The box 211 is assembled to the base 12 in a mode in which an upper end edge of the box 211 is fitted into a rectangular opening provided on the base 12. The tube 212 is a cylindrical container with an open upper surface and stores a cell culture solution containing cellular aggregates and foreign substances. The lid member 213 is a member for blocking the opening of the tube 212. When a dispensing operation is not being performed, the opening of the tube 212 is covered by the lid member 213 in order to prevent dust and the like from entering the tube 212.

A movement of the lid member 213 is realized by adsorption and adsorption release operations of the lid member 213 by a suction disk head 38 (FIG. 7) which is mounted to the second nozzle 37 and by a movement operation of the head section 32. Specifically, during closing of the lid, as shown in FIG. 4, the head section 32 is moved to above the lid member 213 arranged adjacent to the left side of the tube 212 and the suction disk head 38 is lowered to adsorb the lid member 213. Next, the suction disk head 38 is raised and the head section 32 (the suction disk head 38) is moved to above the tube 212. Subsequently, the suction disk head 38 is lowered and adsorption of the lid member 213 is released. A reverse operation of the above is performed during opening of the lid. This operation is applied to movement operations of the lid members of the respective sections of the cell movement line 20 to be described below.

The dispensing tip stocking section 22 is a part which stores a plurality of dispensing tips 80. With reference to FIGS. 7 and 11C, the dispensing tip 80 is an elongated tubular member and includes an upper end section 81 to be fitted into the first nozzle 36, a lower end section 82 with an end edge provided with an opening that suctions and discharges the cell culture solution, and an intermediate section 83 extending between the upper end section 81 and the lower end section 82. The intermediate section 83 has a tapered shape whose outer diameter gradually decreases from a side of the upper end section 81 toward a side of the lower end section 82. The dispensing tip 80 is attachable to and detachable from the first nozzle 36. As described earlier, the first nozzle 36 is a nozzle capable of generating a suction force and a discharge force, and the dispensing tip 80 suctions the cell culture solution when imparted with the suction force and discharges the suctioned cell culture solution when imparted with the discharge force.

The dispensing tip stocking section 22 includes a holding box 221 and a box lid member 223. The holding box 221 holds dispensing tips 80 which are arranged in a matrix pattern in an erected state. A holder member 222 for maintaining the arrangement of the dispensing tips 80 is arranged inside the holding box 221. The dispensing tips 80 are held in the holding box 221 in a state where the upper end sections 81 thereof protrude upward from an upper end surface of the holding box 221. In other words, the dispensing tips 80 are held in the holding box 221 in a state where the dispensing tips 80 can be readily attached to the first nozzle 36 moving in the Z direction. The box lid member 223 is a lid member which is placed on the upper end surface of the holding box 221 to cover and hide the dispensing tips 80.

The cell selecting section 23 is a part which is arranged at a center position in the X direction on the cell movement line 20 and which is used to select a cellular aggregate of a desired size from a cell culture solution containing cellular aggregates of various sizes and foreign substances. The cell selecting section 23 includes a dish 60 (a first container section), a holding table 231, and a table lid member 232. The dish 60 is a container having an opened upper surface into which a cell culture solution containing a cellular aggregate is dispensed by the dispensing tip 80 and which is capable of storing the cell culture solution. The holding table 231 is placed on the base 12 and positions and holds the dish 60. The table lid member 232 is a lid member for covering and hiding the upper surfaces of the dish 60 and the holding table 231. Alternatively, a lid member that only covers the dish 60 may be used instead of the table lid member 232.

FIG. 5 is a perspective view of the dish 60. The dish 60 includes a well plate 61, a petri dish (schale) 62, and a cover member 63. The well plate 61 is a square plate in a top view for carrying a cellular aggregate of a desired size. The petri dish 62 is a container which is constituted by a shallow flat dish having an opened upper surface and which collects a cell culture solution containing small cellular aggregates which are not of the desired size and foreign substances. The well plate 61 is held near a bottom surface of a central portion of the petri dish 62. The cover member 63 is a member having an open lower surface and which includes a cylindrical section 631 with an inner diameter that is larger than an outer diameter of the petri dish 62 and a disk-shaped lid section 632 that blocks an upper end of the cylindrical section 631. The cover member 63 is placed on the petri dish 62 so that the lid section 632 covers the upper surface opening of the petri dish 62. A through-hole 633 is bored through the lid section 632. Through the through-hole 633, a liquid (a cell culture solution) can be injected into a cavity of the petri dish 62 and a liquid can be sucked out from the petri dish 62. In the present embodiment, the dish 60 is formed by a translucent member such as transparent plastic or transparent glass.

An opening 63H is provided at a center of the lid section 632. The opening 63H is a square opening that is larger than the well plate 61. The cover member 63 includes four trapezoidal inclined plates 64 which respectively incline downward and extend toward a cylindrical center of the dish 60 from four sides that define the opening 63H. Lower end edges of the inclined plates 64 are respectively positioned near respective end sides of the well plate 61. A band-like meshed opening 65 is provided near a lower end of the inclined plates 64. The meshed opening 65 is constituted by a plurality of holes that penetrate the inclined plates 64 and communicate the cavity of the petri dish 62 and an internal space defined by the four inclined plates 64 to each other. A mesh size of the meshed opening 65 is selected so as to prevent a cellular aggregate of a desired size from passing through but allow small cellular aggregates which are not of the desired size and foreign substances to pass through.

Figure 6A:
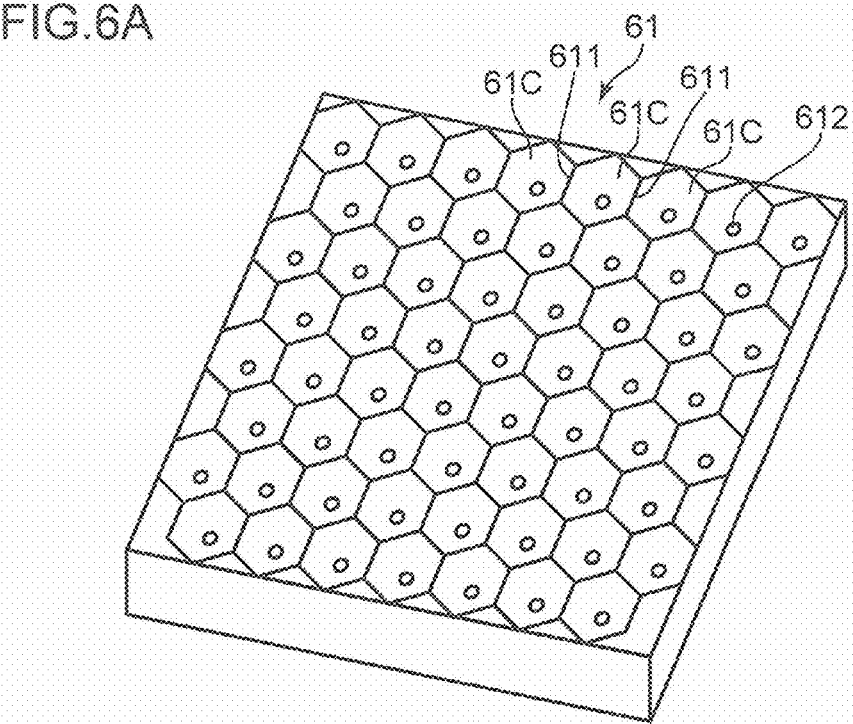
FIG. 6A is a perspective view of a well plate provided in the dish and FIG. 6B is a sectional view for explaining a cell selection operation at the dish.
Figure 6B:
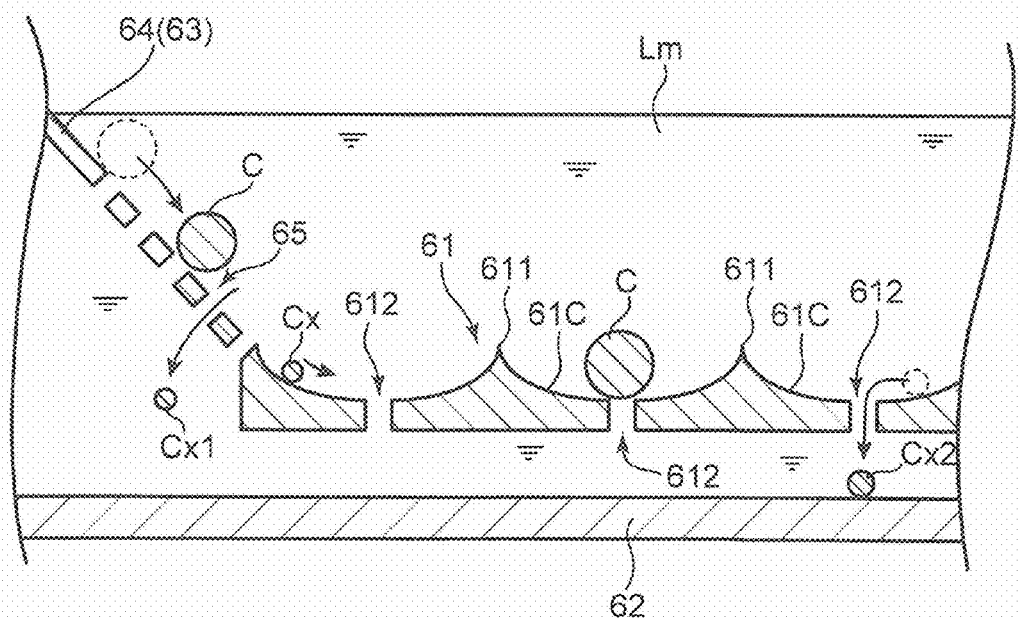

FIG. 6A is a perspective view of the well plate 61 and FIG. 6B is a sectional view which is taken along line VIA-VIA in FIG. 5 and which will be used for explaining a cell selection operation at the dish 60. The well plate 61 includes, on an upper surface side, a plurality of recessed sections 61C for carrying a cellular aggregate. While each recessed section 61C has a semispherical cavity, an upper end opening edge 611 thereof is a hexagon. The plurality of recessed sections 61C are arranged in a honeycomb pattern in a mode where respective upper end opening edges 611 are adjacent to each other. As shown in FIG. 6B, a curvature of the recessed section 61C is relatively small near a bottom section and relatively large near the upper end opening edge 611. Therefore, a ridge section which is formed when upper end opening edges 611 of adjacent recessed sections 61C come into contact with each other is formed by sharp protruding distal end sections.

A release hole 612 that penetrates the well plate 61 in the vertical direction is bored through each recessed section 61C. The release hole 612 is arranged at a central section (a deepest section) of the recessed section 61C. A size of the release hole 612 is selected so as to prevent a cellular aggregate of a desired size from passing through but allow small cellular aggregates which are not of the desired size and foreign substances to pass through. Each recessed section 61C is intended to accommodate one cellular aggregate. A gap with a prescribed height is provided between a rear surface of the well plate 61 and an inner bottom surface of the petri dish 62.

When a cell selection operation is performed, a cell culture solution Lm not containing a cellular aggregate C is injected into the petri dish 62 through, for example, the through-hole 633. As shown in FIG. 6B, a liquid level of the cell culture solution Lm is set to a liquid level which causes the well plate 61 and the meshed opening 65 of the inclined plates 64 to be immersed. Subsequently, a cell culture solution containing the cellular aggregate C to be an extraction object and inevitably mixed-in foreign substances Cx is injected from the opening 63H of the lid section 632. In this case, the cellular aggregate C of the desired size is unable to pass through the meshed opening 65 and is guided to above the well plate 61. On the other hand, the foreign substances Cx pass through the meshed opening 65 and are collected on the petri dish 62 (Cx1). Even if the foreign substances Cx are not trapped by the meshed opening 65 and penetrates into the recessed section 61C of the well plate 61, the foreign substances Cx fall through the release hole 612 to be collected on the petri dish 62 (Cx2).

Since selection of the cellular aggregate C and the foreign substances Cx is performed as described above, only the cellular aggregate C remains on the well plate 61. However, there may be cases where a plurality of cellular aggregates C are carried by one recessed section 61C. When this poses a problem, the holding table 231 is desirably equipped with a mechanism that vibrates the well plate 61. By applying horizontal vibration in the X and Y directions to the holding table 231, the cellular aggregates C carried by one recessed section 61C so as to overlap each other can be readily moved to another recessed section 61C. This is made possible by the fact that a curved surface of the recessed section 61C is an almost-flat gentle curved surface near the bottom section but a relatively steep curved surface near the upper end opening edge 611. As described earlier, since the dish 60 is formed by a transparent member and the base 12 is also translucent, an image of the cellular aggregate C being carried by the recessed section 61C can be captured by the camera 51 under the light of the illuminator 41.

The tip stocking section 24 is a part which is arranged adjacent to the left side of the cell selecting section 23 and which holds a plurality of cylinder tips 70 (an example of a tip). As shown in FIG. 7, the cylinder tip 70 is an elongated tubular member which is attachable to and detachable from the rod section 35 of the head section 32. The cylinder tip 70 performs functions of suctioning a cellular aggregate carried by the recessed section 61C of the well plate 61 described above, transporting the cellular aggregate in accordance with a movement of the head section 32, and discharging the cellular aggregate to the cell transferring section 26.

The tip stocking section 24 includes a holding box 241 and a box lid member 243. The holding box 241 holds cylinder tips 70 arranged in a matrix pattern in an erected state. A holder member 242 for maintaining the arrangement of the cylinder tips 70 is arranged inside the holding box 241. The cylinder tips 70 are held in the holding box 241 in a state where the upper end sections thereof protrude upward from an upper end surface of the holding box 241. In other words, the cylinder tips 70 are held in the holding box 241 in a state where the cylinder tips 70 can be readily attached to the rod section 35 moving in the Z direction. The box lid member 243 is a lid member which is placed on the upper end surface of the holding box 241 to cover and hide the cylinder tips 70.

FIG. 8 is a sectional view showing internal structures of the cylinder tip 70 and the rod section 35. FIG. 8 shows the Z direction, where a +Z direction represents an upper side and a −Z direction represents a lower side of an actual device. The cylinder tip 70 includes a syringe 71 internally provided with a tubular passage 71P that acts as a suction path for suctioning a cellular aggregate and a plunger 72 which reciprocates inside the tubular passage 71P while being in sliding contact with an inner peripheral wall of the syringe 71 that defines the tubular passage 71P.

The syringe 71 includes a syringe base end section 711 which is constituted by a large-diameter cylindrical body, a syringe main body section 712 which is constituted by an elongated small-diameter cylindrical body, and a tapered cylinder section 713 which connects the base end section 711 and the main body section 712 to each other. The tubular passage 71P is formed in the syringe main body section 712. A suction port 71T (which doubles as a discharge port) is provided at a distal end of the syringe main body section 712. The plunger 72 includes a plunger base end section 721 constituted by a cylindrical body, a needle-like plunger main body section 722, and a semispherical section 723 which connects the base end section 721 and the main body section 722 to each other.

The syringe base end section 711 includes a cylindrical hollow section 71H. An outer diameter of the plunger base end section 721 is set smaller than an inner diameter of the hollow section 71H by a prescribed length. An outer diameter of the plunger main body section 722 is set slightly smaller than an inner diameter of the tubular passage 71P. In addition, a shape of an inner peripheral surface of the tapered cylinder section 713 conforms to a curved surface shape of an outer peripheral surface of the semispherical section 723. The plunger 72 is assembled to the syringe 71 in a state in which the plunger base end section 721 is housed inside the hollow section 71H and the plunger main body section 722 is inserted into the tubular passage 71P of the syringe main body section 712.

FIG. 8 shows a state where the plunger main body section 722 is most deeply inserted into the syringe main body section 712 or, in other words, a state where the plunger 72 is at a lowermost position. At this point, a state is created where the semispherical section 723 is completely received in a cavity of the tapered cylinder section 713. A length of the plunger main body section 722 is slightly longer than that of the syringe main body section 712 and, in the state shown in FIG. 8, a distal end section 724 protrudes from the suction port 71T. In addition, a gap exists between an inner peripheral surface of the syringe base end section 711 and an outer peripheral surface of the plunger base end section 721.

The plunger 72 can move in the +Z direction (upward) with respect to the syringe 71 from the state shown in FIG. 8. When the plunger 72 moves in the +Z direction by a prescribed length, the distal end section 724 of the plunger main body section 722 becomes buried inside the tubular passage 71P. At this point, a suction force can be generated in the suction port 71T to suction a liquid (in the present embodiment, a cell culture solution) around the suction port 71T into the tubular passage 71P. By moving the plunger 72 in the −Z direction (downward) after the suction, the liquid suctioned into the tubular passage 71P can be discharged from the suction port 71T.

The rod section 35 includes a columnar rod 351 which is movable in the Z direction (vertical direction), a cylindrical movable cylinder 352 which is arranged around the rod 351 and which is movable in the Z direction, and a cylindrical fixed cylinder 353 which is arranged around the movable cylinder 352. In addition, the rod section 35 is capable of moving in the Z direction as a whole.

The plunger base end section 721 includes an attachment hole 72H which has an opening on an end surface in the +Z direction and which is constituted by a cylindrical hollow space. The attachment hole 72H is a hole for press-fitting a distal end of the rod 351 and, as a result of the press-fitting, the rod 351 and the plunger 72 become integrally movable in the Z direction. The movable cylinder 352 is movable in the Z direction independent of the rod 351. A −Z direction end surface of the movable cylinder 352 opposes a +Z direction end surface of the plunger base end section 721. The fixed cylinder 353 is a cylinder into which the syringe base end section 711 is press-fitted and, during the press-fitting, the fixed cylinder 353 penetrates into a gap between the syringe base end section 711 and the plunger base end section 721.

Next, suction and discharge operations of the cellular aggregate C by the cylinder tip 70 will be described with reference to FIGS. 9A to 9E. A case will be described where the cellular aggregate C existing in a cell culture solution Lm1 stored in a container C1 is suctioned by the cylinder tip 70 and the cellular aggregate C is discharged into the cell culture solution Lm1 stored in a container C2. When applied to the present embodiment, the container C1 is a container arranged in the cell selecting section 23 and the container C2 is a container arranged in the cell transferring section 26.

As shown in FIG. 9A, the cylinder tip 70 is moved to directly above the cellular aggregate C that is a suction subject. In a state where the plunger 72 has moved relatively upward (+Z direction) with respect to the syringe 71 and a distal end section 724 of the plunger main body section 722 has been buried into the syringe main body section 712, as shown in FIG. 9B, the plunger 72 is moved to a lowermost position (in the −Z direction) and the distal end section 724 is caused to protrude from the suction port 71T. In other words, a state is created where no air exists inside the tubular passage 71P of the syringe main body section 712. Subsequently, as shown in FIG. 9C, the cylinder tip 70 is lowered as a whole and the suction port 71T is thrust into the cell culture solution Lm1 in the container C1. At this point, the suction port 71T is brought as close to the cellular aggregate C as possible.

Next, as shown in FIG. 9D, the plunger 72 is moved upward by a prescribed height. Due to this operation, a suction force is generated in the suction port 71T and the cellular aggregate C and a part of the cell culture solution Lma are suctioned into the syringe main body section 712. In this state, the cylinder tip 70 is raised as a whole and moved to an arrangement position of the container C2. Subsequently, as shown in FIG. 9E, the cylinder tip 70 is lowered as a whole until the suction port 71T is thrust into the cell culture solution Lm2 in the container C2. Next, the plunger 72 at the prescribed height position is lowered until the distal end section 724 protrudes from the suction port 71T. Due to this lowering operation, the cellular aggregate C is discharged into the cell culture solution Lm2 in the container C2.

Returning to FIG. 4, the tip imaging section 25 is a pit which provides a position where an image of the cylinder tip 70 attached to the rod section 35 is to be captured. An arrangement position of the tip imaging section 25 is between the cell selecting section 23 and the tip stocking section 24. In the present embodiment, the imaging is performed by the imaging unit 50 (a tip imaging device). Therefore, when the imaging is performed, the camera 51 of the imaging unit 50 is moved to directly below the tip imaging section 25 and an image of each cylinder tip 70 is captured under the illumination of the vertical illuminator 52. Based on an image of the cylinder tip 70 and focal position information at the time of the imaging, an XYZ coordinate position of the suction port 71T of the cylinder tip 70 is determined. A correction value is derived from a difference between the coordinate position and a reference position determined in advance. The correction value is used as a correction value during movement control of the rod section 35 (the head section 32).

The cell transferring section 26 is a part which is arranged near a downstream-side end in the X direction of the cell movement line 20 and which acts as a movement destination of a cellular aggregate suctioned from the dish 60 of the cell selecting section 23. The cell transferring section 26 includes a microplate 90 (a second container section), a holding table 261, and a table lid member 262.

The microplate 90 is a plate on which a large number of small wells 91 with opened upper surfaces are arranged in a matrix pattern. The microplate 90 is formed by a translucent member such as transparent plastic. One cellular aggregate is accommodated in one well 91. Therefore, an image of a cellular aggregate in a state where the cellular aggregate is accommodated in each well 91 can be captured by the camera 51. In addition, an arrangement pitch of the wells 91 is set approximately the same as an arrangement pitch of the group of cylinder tips 70 attached to the rod sections 35 arranged in a single row. Accordingly, cellular aggregates can be simultaneously discharged from the group of cylinder tips 70 to the wells 91. The holding table 261 is placed on the base 12 and positions and holds the microplate 90. The table lid member 262 is a lid member for covering and hiding the upper surfaces of the microplate 90 and the holding table 261.

The black cover mounting section 27 is a part on which a first black cover 271 to be placed on the cell transferring section 26 and a second black cover 272 to be placed on the cell selecting section 23 are mounted. In consideration of such covering objects, the black cover mounting section 27 is arranged between the cell selecting section 23 and the cell transferring section 26. The first and second black covers 271 and 272 are light-shielding bodies used when capturing an image of a cellular aggregate carried by the dish 60 or the microplate 90 in a state where light is shielded. The first and second black covers 271 and 272 are boxes which have openings on their lower surfaces and which conform to external sizes of the holding tables 231 and 261. For example, when a fluorescent agent is added to a cell culture solution to perform a fluorescent observation of a cellular aggregate, the first and second black covers 271 and 272 are placed so as to cover and hide the holding tables 231 and 261.

The tip discarding section 28 is a part which is arranged at a most downstream side end section in the X direction of the cell movement line 20 and at which used cylinder tips 70 and dispensing tips 80 after completing the suction and discharge operations described earlier are discarded. The tip discarding section 28 includes a collection box 281 for housing the cylinder tips 70 and the dispensing tips 80 after use. When discarding, the head section 32 equipped with the cylinder tip 70 or the dispensing tip 80 is moved to above an opening 282 of the collection box 281 and a detachment operation of the cylinder tip 70 or the dispensing tip 80 from the head section 32 is executed. Due to this detachment operation, the cylinder tip 70 or the dispensing tip 80 drops into the collection box 281 through the opening 282.

FIGS. 10A and 10B are partially-cutaway perspective views for explaining an attaching/detaching operation of the cylinder tip 70 to/from the rod section 35. In the drawings, the plunger 72 of the cylinder tip 70 has been omitted for the sake of simplicity. When attaching the cylinder tip 70, the head section 32 is moved to above the tip stocking section 24 and one rod section 35 having been positioned with respect to one cylinder tip 70 is lowered. At this point, as shown in FIG. 10A, a lower end surface of the rod 351 and a lower end surface of the fixed cylinder 353 are set approximately flush with each other while a lower end surface 352L of the movable cylinder 352 is placed in an upward-buried state with respect to the lower end surfaces of the rod 351 and the fixed cylinder 353. The buried length is equal to or greater than a Z direction length of the plunger base end section 721 of the plunger 72.

The lowering of the rod section 35 in the state described above causes the rod 351 to be press-fitted into the attachment hole 72H (FIG. 8) of the plunger base end section 721 and the fixed cylinder 353 to be press-fitted into the hollow section 71H of the syringe base end section 711. Accordingly, the attachment of the rod section 35 to the cylinder tip 70 is completed. By vertically moving only the rod 351 in this state, the plunger 72 can be reciprocated with respect to the syringe 71.

When detaching the cylinder tip 70, the head section 32 is moved to above the tip discarding section 28. Subsequently, as shown in FIG. 10B, the movable cylinder 352 having been retreated above is lowered. Accordingly, the plunger base end section 721 is pressed downward by the lower end surface 352L of the movable cylinder 352 and the plunger base end section 721 starts to fall out from the rod 351. As a result, the semispherical section 723 of the plunger 72 starts to press an inner peripheral surface 713T of the tapered cylinder section 713 of the syringe 71 and a pressing force that causes the syringe 71 to fall out from the fixed cylinder 353 starts to act on the syringe 71. When the movable cylinder 352 is further lowered, the cylinder tip 70 eventually falls out from the rod section 35 and is received by the collection box 281.

FIGS. 11A to 11D are perspective views for explaining an attaching/detaching operation of the dispensing tip 80 to/from the first nozzle 36. A guiding arm 361 is annexed to the first nozzle 36. The guiding arm 361 includes a guiding recess 362 which is opened to the side and which has an opening width that is slightly larger than an outer diameter of the first nozzle 36. The first nozzle 36 vertically moves in a state of being housed in a cavity of the guiding recess 362.

When attaching the dispensing tip 80, the head section 32 is moved to above the dispensing tip stocking section 22 and the first nozzle 36 having been positioned with respect to one dispensing tip 80 is lowered. Due to the lowering, as shown in FIG. 11B, a lower end 36L of the first nozzle 36 fits into the upper end section 81 of the dispensing tip 80. Since the intermediate section 83 below the upper end section 81 of the dispensing tip 80 has a tapered shape, when the first nozzle 36 fits into the dispensing tip 80 by a prescribed length, the first nozzle 36 and the dispensing tip 80 become substantially coupled to each other. In other words, a cylinder space of the first nozzle 36 and a tube internal space of the dispensing tip 80 become tightly coupled to each other. Therefore, when the first nozzle 36 generates a suction force, a liquid can be suctioned from an opening at the lower end section 82 of the dispensing tip 80. On the other hand, when the first nozzle 36 generates a discharge force, the suctioned liquid can be discharged from the opening at the lower end section 82.

When detaching the dispensing tip 80, the head section 32 is moved to above the tip discarding section 28. Subsequently, as shown in FIG. 11C, the first nozzle 36 in a state where the dispensing tip 80 is attached thereto is pulled upward. When pulling of the first nozzle 36 proceeds to a certain point, a lower end surface of the guiding arm 361 and an upper end edge of the dispensing tip 80 start interfering with each other. Due to the interference, the dispensing tip 80 gradually detaches from the first nozzle 36, and the dispensing tip 80 eventually falls out of the first nozzle 36 to be received by the collection box 281.

FIGS. 12A and 12B are perspective views of the second nozzle 37 and the suction disk head 38. The second nozzle 37 includes a syringe pipe 371 and a piston 372 which is housed in the syringe pipe 371 and which reciprocates in the vertical direction. In the drawings, a vicinity of a lower end 371L of the syringe pipe 371 is shown cut away. A piston head 373 is attached to a lower end of the piston 372 and a clad pipe 37A is attached to the lower end 371L of the syringe pipe 371. The suction disk head 38 is attached to the clad pipe 37A so as to block a lower end opening of the clad pipe 37A. Note that a suction port is provided at a central section of the suction disk head 38 and an internal space of the clad pipe 37A is communicated with the outside through the suction port.

As shown in FIGS. 12A and 12B, the second nozzle 37 is vertically movable as a whole. In addition, the piston 372 is independently vertically movable. With a vertical movement of the piston 372, the piston 372 vertically moves inside the clad pipe 37A of the piston head 373. In accordance with the vertical movement, a suction force or a discharge force is generated at the suction port of the suction disk head 38. In other words, raising of the piston 372 creates negative pressure inside the clad pipe 37A and generates a suction force, and lowering of the piston 372 generates a discharge force.

A usage example of the suction disk head 38 will be described. For example, the second nozzle 37 is arranged on the table lid member 232 of the cell selecting section 23 (FIG. 4) and the second nozzle 37 is lowered so that the suction disk head 38 comes into contact with an upper surface of the table lid member 232. Next, the piston 372 is raised to generate a suction force and the table lid member 232 is adsorbed. Then, the second nozzle 37 is raised and moved to above the holding table 231. Subsequently, the second nozzle 37 and the piston 372 are lowered to release the adsorption. Accordingly, the dish 60 is covered by the table lid member 232. This similarly applies to other lid members.

Figure 29:
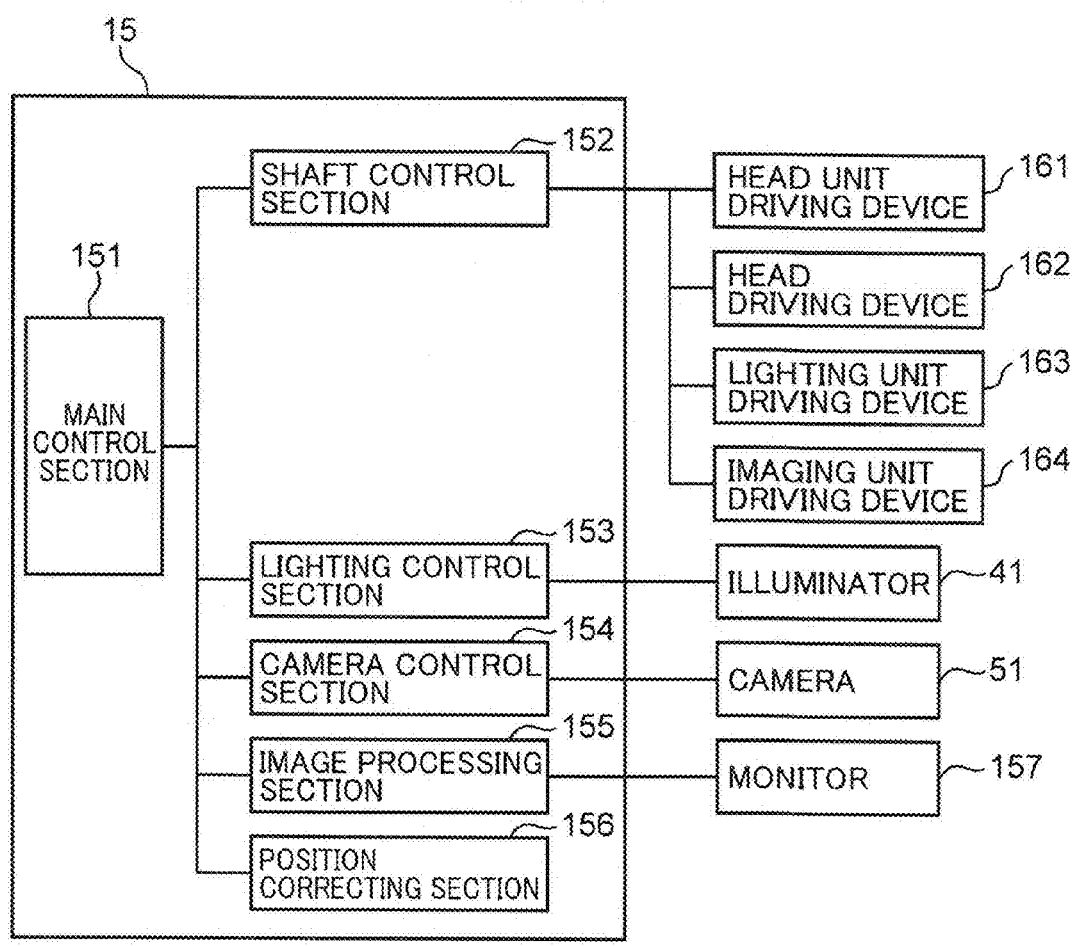
FIG. 29 is a block diagram showing a configuration of a control section of the moving device.

FIG. 29 is a block diagram showing a configuration of the control section 15 of the moving device 1. The control section 15 functionally includes a main control section 151, a shaft control section 152 (a drive control section), a lighting control section 153, a camera control section 154, an image processing section 155, and a position correcting section 156. The main control section 151 comprehensively performs various controls in the device main body 10 of the moving device 1. In other words, as schematically shown in FIG. 4, the main control section 151 moves the head unit 30 (the head section 32) in the XY directions towards the respective sections of the cell movement line 20, performs attachment and detachment operations of the cylinder tip 70 or the dispensing tip 80 and suction and discharge operations of a cell culture solution (a cellular aggregate), and moves the lighting unit 40 (the illuminator 41) and the imaging unit 50 (the camera 51) in the X direction to capture images of a cellular aggregate carried by the dish 60 or the microplate 90 or to capture images of the cylinder tip 70 attached to the rod section 35.

The shaft control section 152 controls operations of the head unit driving device 161, the head driving device 162, the lighting unit driving device 163, and the imaging unit driving device 164. Specifically, due to control of the head unit driving device 161, movements of the head unit 30 in the X-Y directions are controlled. Due to control of the head driving device 162, vertical movements of the rod sections 35, the first nozzle 36, and the second nozzle 37, raising and lowering operations of the rod 351 and the like at the rod sections 35 (suction and discharge operations), suction and discharge operations at the first nozzle 36 and the second nozzle 37, and the like are controlled. Due to control of the lighting unit driving device 163, movements of the lighting unit 40 in the X direction are controlled. Due to control of the imaging unit driving device 164, movements of the imaging unit 50 in the X direction are controlled.

The lighting control section 153 controls light-emitting operations of the illuminator 41. Specifically, the lighting control section 153 causes the illuminator 41 to be turned on and off according to a prescribed routine in order to generate transmissive illumination when an image of a cellular aggregate held by the cell selecting section 23 or the cell transferring section 26 is captured by the imaging unit 50.

The camera control section 154 controls imaging operations by the camera 51. For example, during the imaging operations, the camera control section 154 controls focusing, a shutter timing, a shutter speed (an exposure amount), and the like of the camera 51.

The image processing section 155 performs image processing such as shading correction and white balance adjustment on images acquired by the camera 51. In the present embodiment, images of cellular aggregates acquired at the cell selecting section 23 or the cell transferring section 26 are subjected to the image processing and displayed on a monitor 157. In addition, the image processing section 155 applies known image processing techniques to a recognition image of the cylinder tip 70 acquired at the tip imaging section 25 to obtain XY position information on the suction port 71T of the cylinder tip 70 attached to the rod section 35.

The position correcting section 156 performs a process of obtaining an XYZ coordinate position of the suction port 71T of the cylinder tip 70 attached to the rod section 35 (attachment position information on the cylinder tip) from XY-direction position information on the suction port 71T as obtained by the image processing section 155 and focal position information in the Z direction of the suction port 71T as determined by a focusing operation of the camera control section 154 (information obtained by an imaging operation). Subsequently, the position correcting section 156 derives a correction value from a difference between the XYZ coordinate position and a reference position determined in advance. The shaft control section 152 refers to the correction value and controls the head unit driving device 161 and the head driving device 162 to cause suction and discharge operations by the cylinder tip 70 to be executed at accurate positions.

Hereinafter, operations by the moving device 1 according to the present embodiment will be described with reference to FIGS. 13 to 29. The control section 15 mainly causes the device main body 10 to execute a dispensing operation (FIGS. 13 to 17) and a cell movement operation (FIGS. 18 to 26). In the dispensing operation, the control section 15 causes the device main body 10 to sequentially execute the following:

(Control 1) Control for moving the head unit 30 to above the dispensing tip stocking section 22 and attaching the dispensing tip 80 to the first nozzle 36;

(Control 2) Control for moving the head unit 30 to above the subject stocking section 21 and suctioning a cell culture solution containing a cellular aggregate which is stored in the tube 212 into the dispensing tip 80 by a prescribed dispensing amount;

(Control 3) Control for moving the head unit 30 to above the cell selecting section 23 and discharging the cell culture solution inside the dispensing tip 80 to the dish 60; and (Control 4) Control for moving the head unit 30 to above the tip discarding section 28, detaching the used dispensing tip 80 from the first nozzle 36, and discarding the used dispensing tip 80 into the collection box 281.

In the cell movement operation, the control section 15 causes the device main body 10 to sequentially execute the following:

(Control 5) Control for moving the head unit 30 to above the tip stocking section 24 and attaching the cylinder tip 70 to the rod section 35 (first control);

(Control 6) Control for moving the head unit 30 to above the cell selecting section 23 and suctioning a cellular aggregate stored in the dish 60 into the cylinder tip 70 (second control);

(Control 7) Control for moving the head unit 30 to above the cell transferring section 26 and discharging the cellular aggregate inside the cylinder tip 70 to the microplate 90 (third control); and (Control 8) Control for moving the head unit 30 to above the tip discarding section 28, detaching the used cylinder tip 70 from the rod section 35, and discarding the used cylinder tip 70 into the collection box 281 (fourth control).

Figure 27:
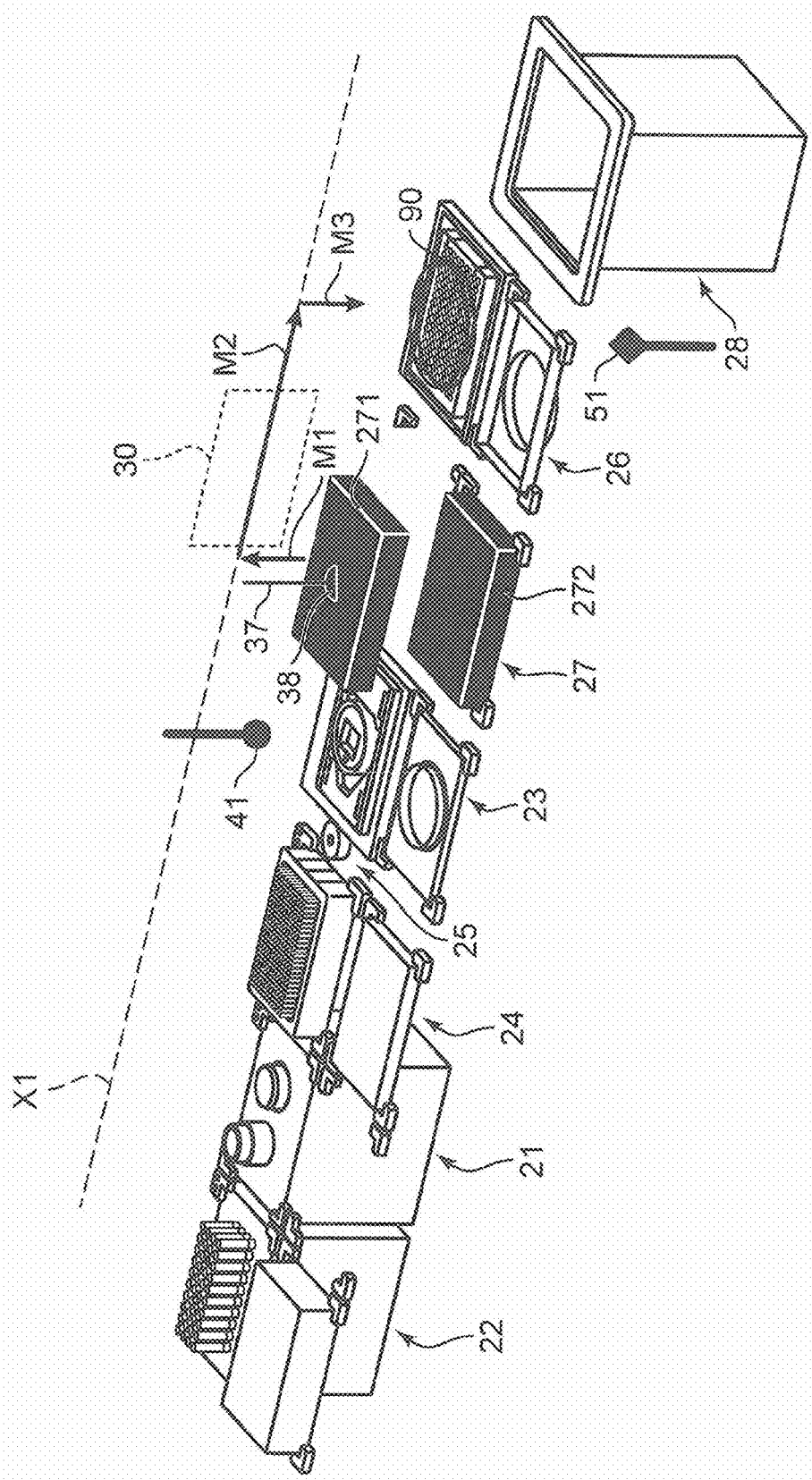
FIG. 27 is a perspective view showing a state of movement of a head section on the cell movement line.
Figure 28:
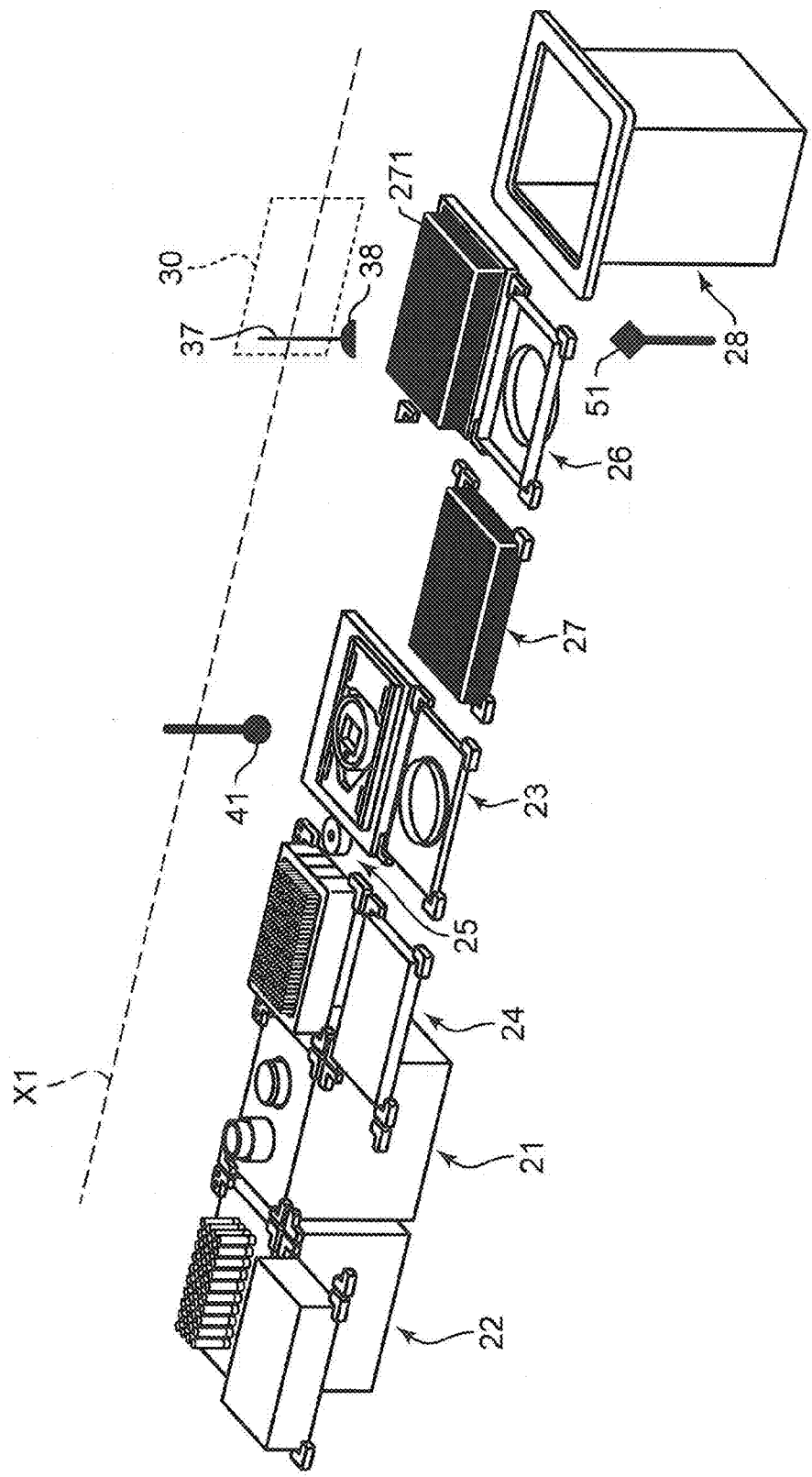
FIG. 28 is a perspective view showing a state of movement of a head section on the cell movement line.

Moreover, when fluorescent photography is to be performed, the control section 15 causes the device main body 10 to execute the following:

(Control 9) Control for moving the head unit 30 to above the black cover mounting section 27, adsorbing, for example, the first black cover 271, and covering the cell transferring section 26 with the first black cover 271 (refer to FIGS. 27 and 28).

Hereinafter, the operations listed above will be described in detail with reference to FIGS. 13 to 29. In the drawings, the X direction will be described as a left-right direction, the Y direction as a front-rear direction, and the Z direction as an up-down direction. In addition, in the drawings, positions of the head unit 30, the illuminator 41 of the lighting unit 40, and the camera 51 of the imaging unit 50 are schematically shown. In the head unit 30, the rod section 35 and the first nozzle 36 of the head section 32 are schematically represented by arrows. Furthermore, a main movement path in the horizontal direction of the head unit 30 is shown as a path X1 by a dotted line and a bypass movement path is shown as a path X2 by a dashed-dotted line. The path X1 is a path that passes directly above the dish 60 and the microplate 90. The lighting unit 40 and the imaging unit 50 also generally move along the path X1. The path X2 is a path that generally passes above the table lid members 232 and 262. The path X2 is exclusively provided in order to avoid interference between the head unit 30 and the lighting unit 40.

First, the dispensing operation will be described with reference to FIGS. 13 to 17 and 29. Moreover, prior to the start of the dispensing operation, various settings of the cell movement line 20 such as replenishing the cylinder tips 70 and the dispensing tips 80, filling the tube 212 with a cell culture solution containing cellular aggregates, and filling the microplate 90 with a reagent have been completed. In addition, preparation such as optical axis adjustment and light amount adjustment of the illuminator 41 and the camera 51 and origin alignment of the head unit 30 have also been completed. Furthermore, the lid members of the respective sections of the cell movement line 20 have been removed.

Figure 13:
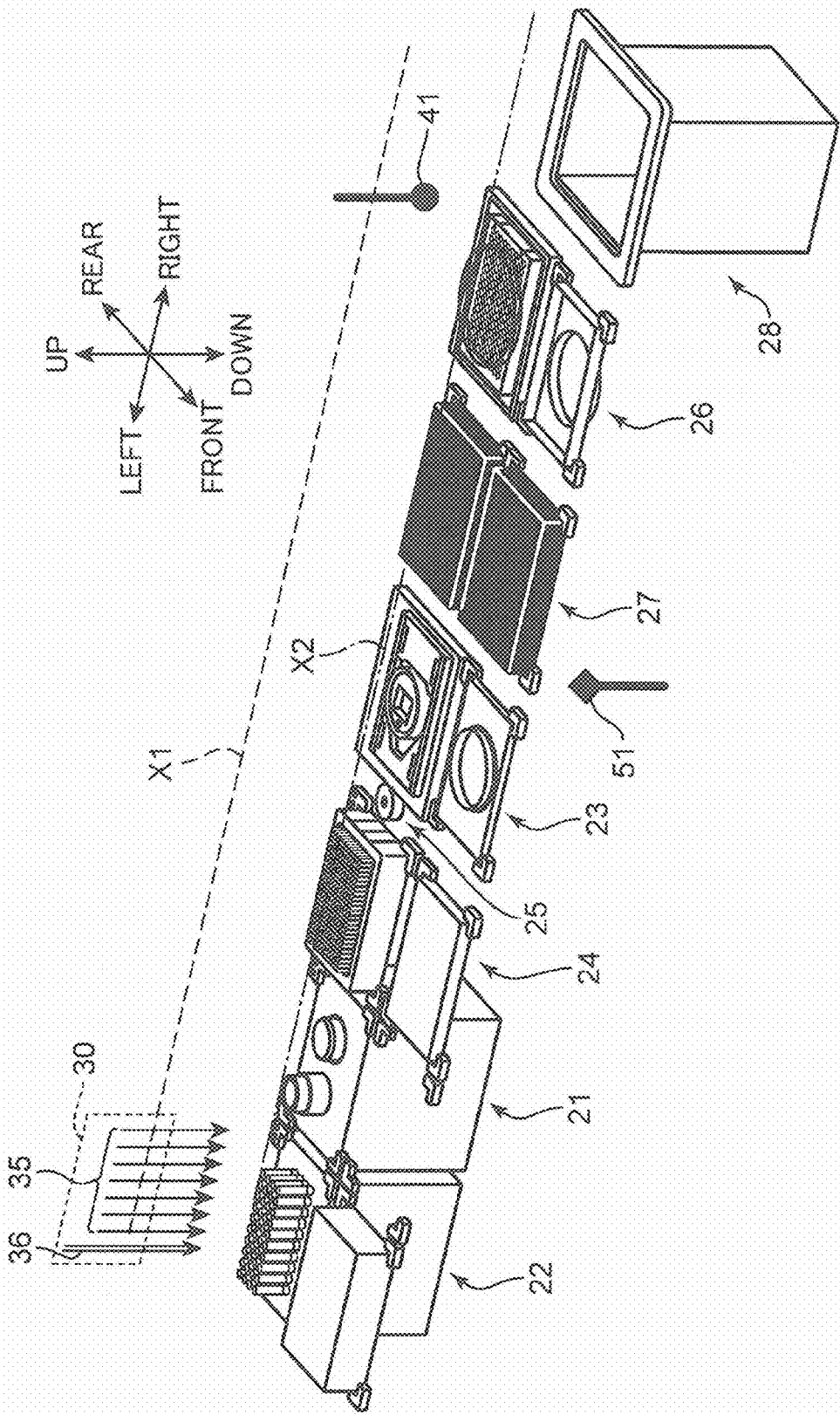
FIG. 13 is a perspective view showing a state of movement of a head section on the cell movement line.

FIG. 13 shows a state immediately prior to the start of the dispensing operation. The head unit 30 is positioned above the dispensing tip stocking section 22 on the path X1. The illuminator 41 is positioned above the tip discarding section 28 and the camera 51 is positioned below the cell selecting section 23. At this point, the first nozzle 36 of the head unit 30 is positioned with respect to one dispensing tip 80 that is an attachment object.

Figure 14:
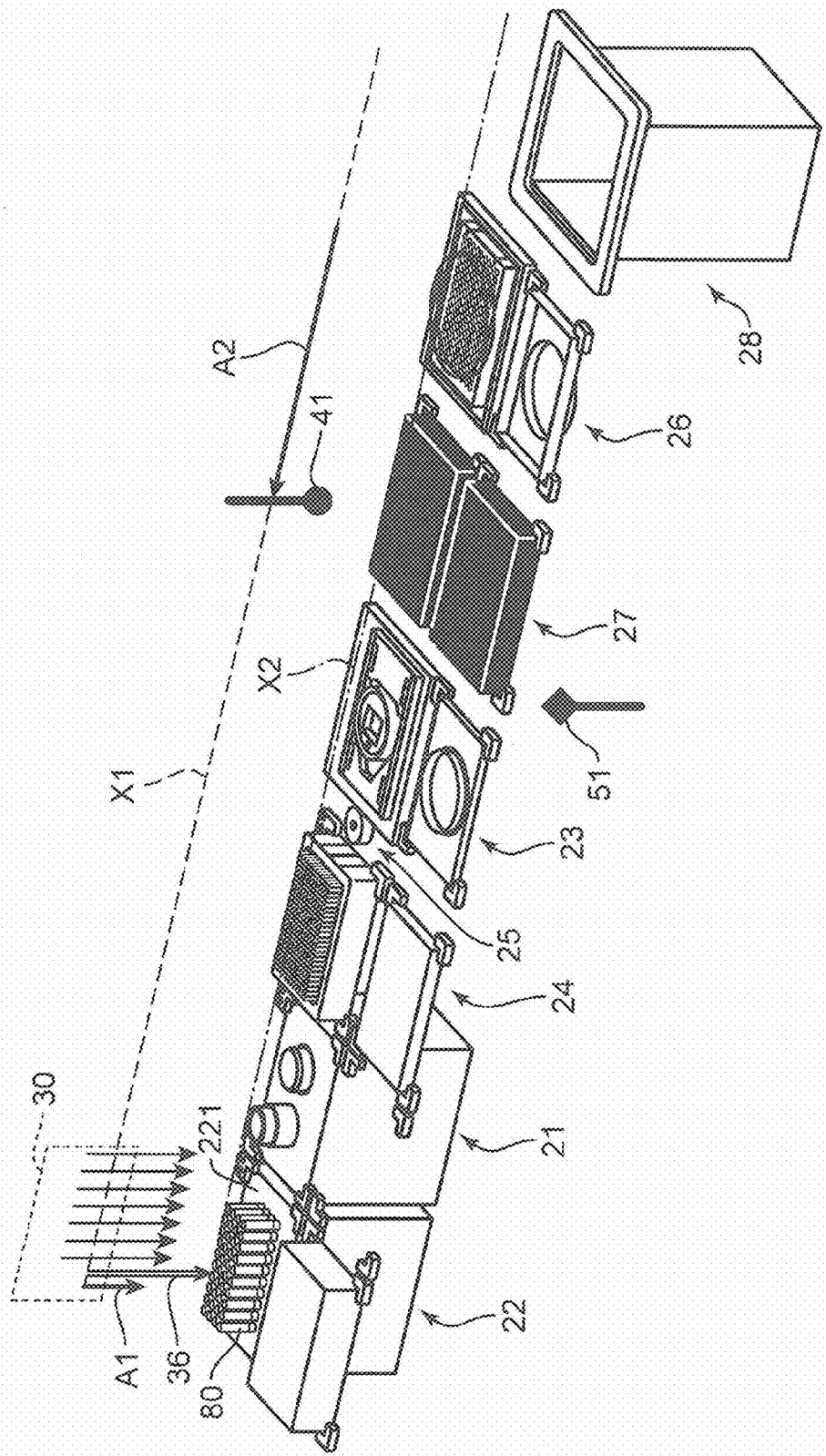
FIG. 14 is a perspective view showing a state of movement of a head section on the cell movement line.

FIG. 14 is a diagram showing a state where "control 1" described above is being executed. As indicated by an arrow A1, the shaft control section 152 controls the head driving device 162 and lowers the first nozzle 36 toward a targeted dispensing tip 80. Due to the lowering, the first nozzle 36 fits into the dispensing tip 80 by a prescribed length and the dispensing tip 80 is attached to the first nozzle 36. At this timing, as indicated by an arrow A2, the shaft control section 152 controls the lighting unit driving device 163 to move the illuminator 41 leftward and stop the illuminator 41 above the black cover mounting section 27. This is an operation for retracting the illuminator 41 so that the head unit 30 and the illuminator 41 do not interfere with each other during an operation for discarding the dispensing tip 80 to the tip discarding section 28 to be performed later.

Figure 15:
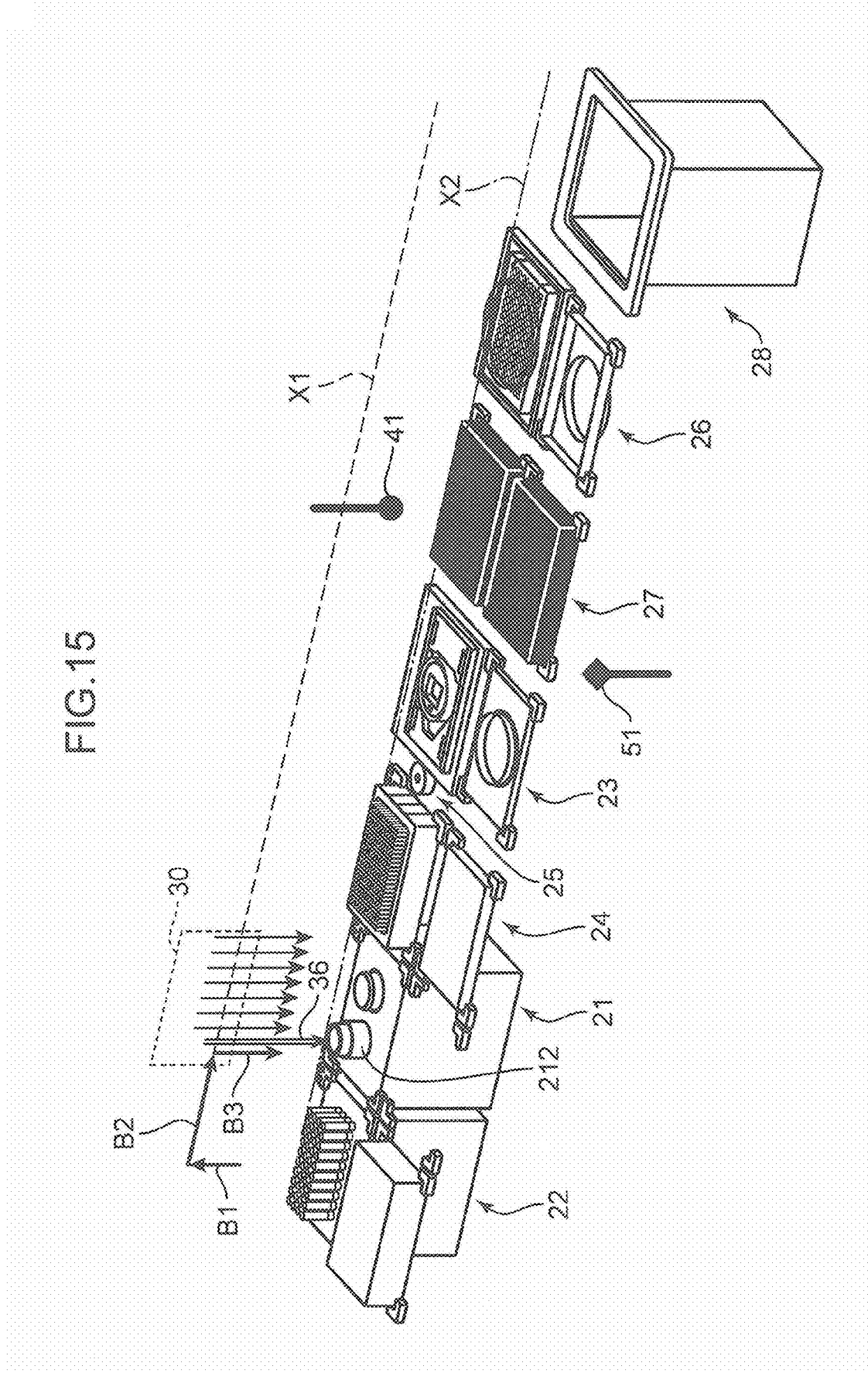
FIG. 15 is a perspective view showing a state of movement of a head section on the cell movement line.

FIG. 15 is a diagram showing a state where "control 2" described above is being executed. From the state shown in FIG. 14, as indicated by an arrow B1, the shaft control section 152 raises the first nozzle 36 to which the dispensing tip 80 has been attached. Next, the shaft control section 152 controls the head unit driving device 161 and, as indicated by an arrow B2, moves the head unit 30 rightward and stops the head unit 30 above the subject stocking section 21. The stop position is a position where the first nozzle 36 is directly above an upper surface opening of the tube 212. Subsequently, as indicated by an arrow B3, the first nozzle 36 is lowered. Due to the lowering, the lower end section 82 (FIG. 11C) of the dispensing tip 80 is immersed into a cell culture solution containing cellular aggregates stored in the tube 212. In addition, the shaft control section 152 controls the head driving device 162 to generate a suction force in the first nozzle 36 and causes the cell culture solution in the tube 212 to be suctioned by the dispensing tip 80 by a prescribed dispensing amount.

Figure 16:
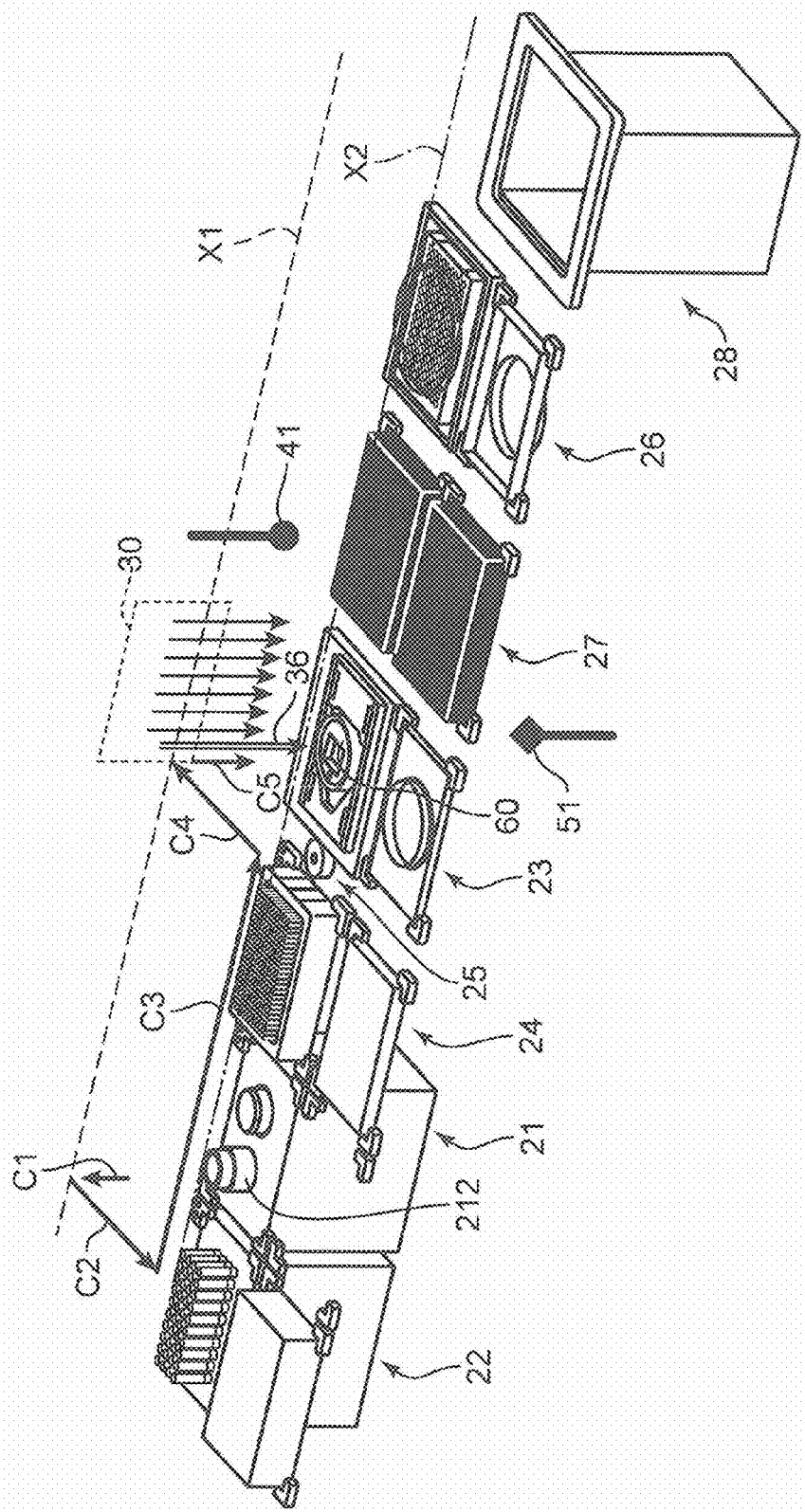
FIG. 16 is a perspective view showing a state of movement of a head section on the cell movement line.

FIG. 16 is a diagram showing a state where "control 3" described above is being executed. First, from the state shown in FIG. 15, as indicated by an arrow C1, the shaft control section 152 raises the first nozzle 36 attached with the dispensing tip 80 having suctioned the cell culture solution. Subsequently, the head unit 30 is moved to above the cell selecting section 23. During the movement, as indicated by arrows C2, C3, and C4, the shaft control section 152 causes the head unit 30 to take a movement path in which the head unit 30 is temporarily moved in a front direction from the path X1 toward the path X2 and, after being moved rightward on the path X2, moved in a rear direction. This is performed in consideration of liquid dripping from the dispensing tip 80 having suctioned the cell culture solution. In other words, if the head unit 30 is to be moved rightward in a straight-forward manner along the path X1 from the state shown in FIG. 15, the head unit 30 is to pass above the tip stocking section 24, creating a concern that the cell culture solution may drip at this point from the lower end section 82 of the dispensing tip 80 onto an unused cylinder tip 70. By having the head unit 30 take the movement path described above, the problem of liquid dripping described above can be resolved. Moreover, in order to prevent liquid dripping itself, an openable and closable cover member that covers the lower end opening of the dispensing tip 80 is desirably annexed to the lower end section 82. Alternatively, a mechanism that controls inner pressure of the dispensing tip 80 may be provided in order to control the inner pressure so that liquid dripping does not occur from the lower end opening.

Once the head unit 30 is stopped above the cell selecting section 23, the shaft control section 152 lowers the first nozzle 36 toward the dish 60 as indicated by an arrow C5. Due to the lowering, the lower end section 82 of the dispensing tip 80 approaches the dish 60 to a prescribed position. Subsequently, the shaft control section 152 causes the first nozzle 36 to generate a discharge force therein and discharge the cell culture solution inside the dispensing tip 80 into the dish 60.

The dispensing operation described above is normally repeated a plurality of times. Generally, the cell culture solution inside the tube 212 eventually separates into a cell suspension portion near a bottom section where cellular aggregates stay and a supernatant liquid portion above the cell suspension portion. On the other hand, when a cell suspension liquid containing a large amount of cellular aggregates is abruptly discharged to an empty dish 60, dispersion of the cellular aggregates with respect to the well plate 61 declines. In consideration thereof, a method is desirably used where the supernatant liquid is first poured into the dish and the cell suspension liquid is subsequently poured. In other words, by pouring the cell suspension liquid after the well plate 61 is immersed into the supernatant liquid, deformation of cells due to liquid flow can be prevented and the cellular aggregates can be efficiently dispersed on the well plate 61.

When adopting this method, in a first dispensing operation (or an initial plurality of dispensing operations), during the lowering operation of the first nozzle 36 indicated by the arrow B3 in FIG. 15, a degree of lowering is reduced and the supernatant liquid is suctioned by the dispensing tip 80 from the tube 212. Discharge of the supernatant liquid inside the dispensing tip 80 to the dish 60 may be performed from either the opening 63H or the through-hole 633 (FIG. 5). After discharging the supernatant liquid, the shaft control section 152 moves the head unit 30 to the subject stocking section 21 on a reverse path to the arrows C2 to C4.

Next, the shaft control section 152 executes an operation for suctioning the cell suspension liquid. In this case, during the lowering operation of the first nozzle 36 indicated by the arrow B3, the degree of lowering is increased so that the lower end section of the dispensing tip 80 reaches near a vicinity of a bottom section of the tube 212. Subsequently, the cell suspension liquid is suctioned by the dispensing tip 80. Next, after moving the head unit 30 on the path indicated by the arrows C2 to C4, the shaft control section 152 causes the dispensing tip 80 to discharge the cell suspension liquid to the dish 60. Since the cellular aggregate must be carried by the well plate 61, the discharge is performed with respect to the opening 63H. Moreover, during the discharge, an operation such as discharging the cell suspension liquid in minute amounts from the dispensing tip 80 or discharging the cell suspension liquid while rocking the dispensing tip 80 by minutely rocking the head unit 30 is desirably performed so that the cellular aggregates are evenly carried by the respective recessed sections 61C of the well plate 61.

Figure 17:
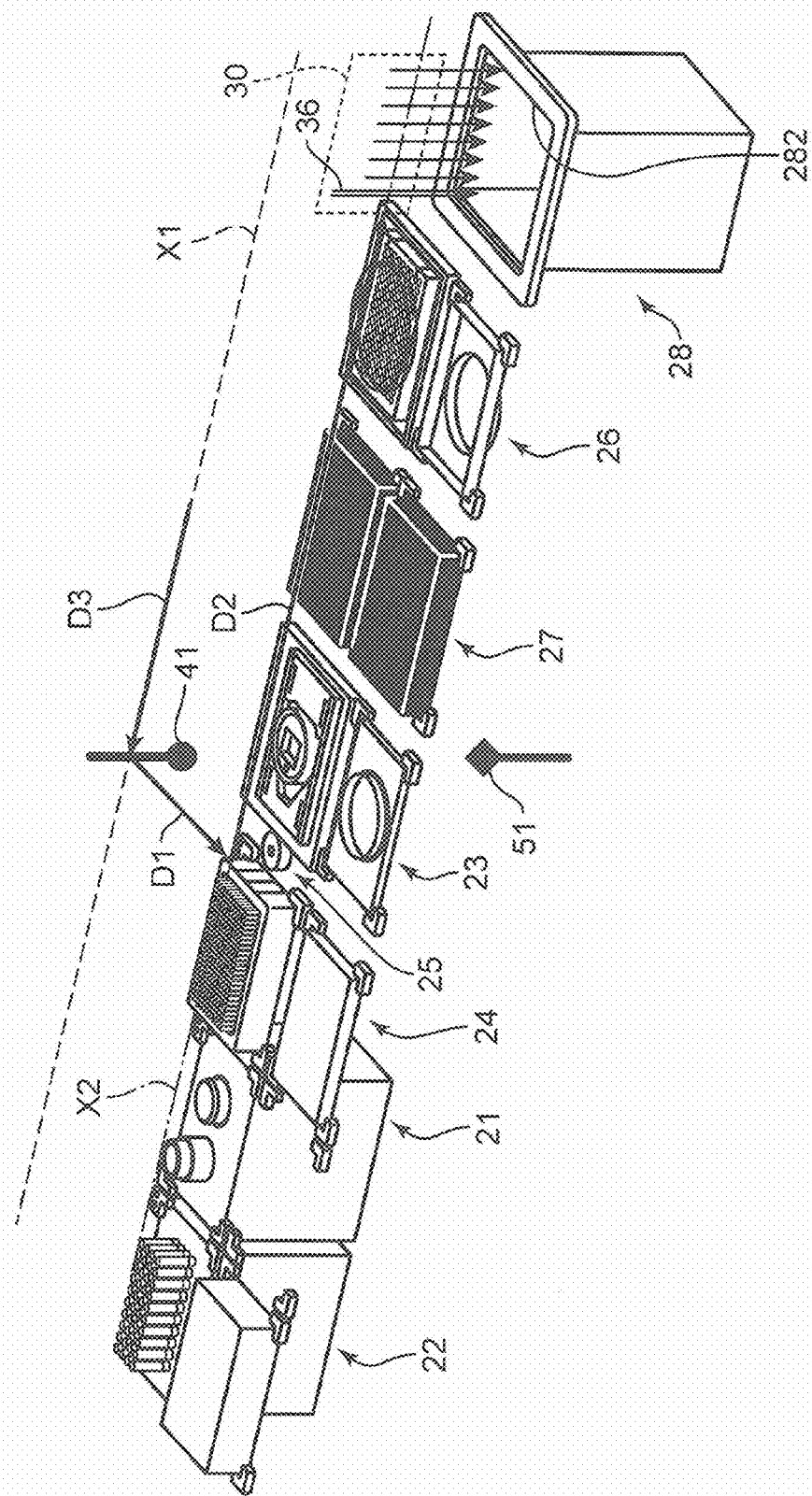
FIG. 17 is a perspective view showing a state of movement of a head section on the cell movement line.

FIG. 17 is a diagram showing a state where "control 4" described above is being executed. After raising the first nozzle 36 attached with the dispensing tip 80 from the state shown in FIG. 16, the shaft control section 152 moves the head unit 30 to above the tip discarding section 28. During the movement, the shaft control section 152 moves the head unit 30 in the front direction from the path X1 toward the path X2 as indicated by an arrow D1 and subsequently moves the head unit 30 rightward on the path X2 as indicated by an arrow D2. After stopping the head unit 30 above the tip discarding section 28, the shaft control section 152 controls the head driving device 162 to detach the dispensing tip 80 from the first nozzle 36 and discard the dispensing tip 80 into the collection box 281 according to the procedure described earlier with reference to FIGS. 11A to 11D.

In the present embodiment, before discarding the dispensing tip 80, an inspection step for checking a carried state of cellular aggregates on the well plate 61 is executed. The inspection step includes a process of capturing an image of the dish 60 (the well plate 61) with the camera 51. To this end, as indicated by an arrow D3, the shaft control section 152 moves the illuminator 41 leftward. In addition, under control of the lighting control section 153 and the camera control section 154, imaging of the well plate 61 is performed by the camera 51 under transmissive illumination by the illuminator 41. Subsequently, image processing on the photographed image is executed by the image processing section 155 and, based on the image, a confirmation is made on whether or not cellular aggregates are favorably carried by the respective recessed sections 61C in a desired state. When a favorable carried state is confirmed, discarding of the dispensing tip 80 is executed. When the carried state is not favorable, means such as re-dispensing the cell suspension liquid or imparting vibration to the dish 60 is employed.

Figure 18:
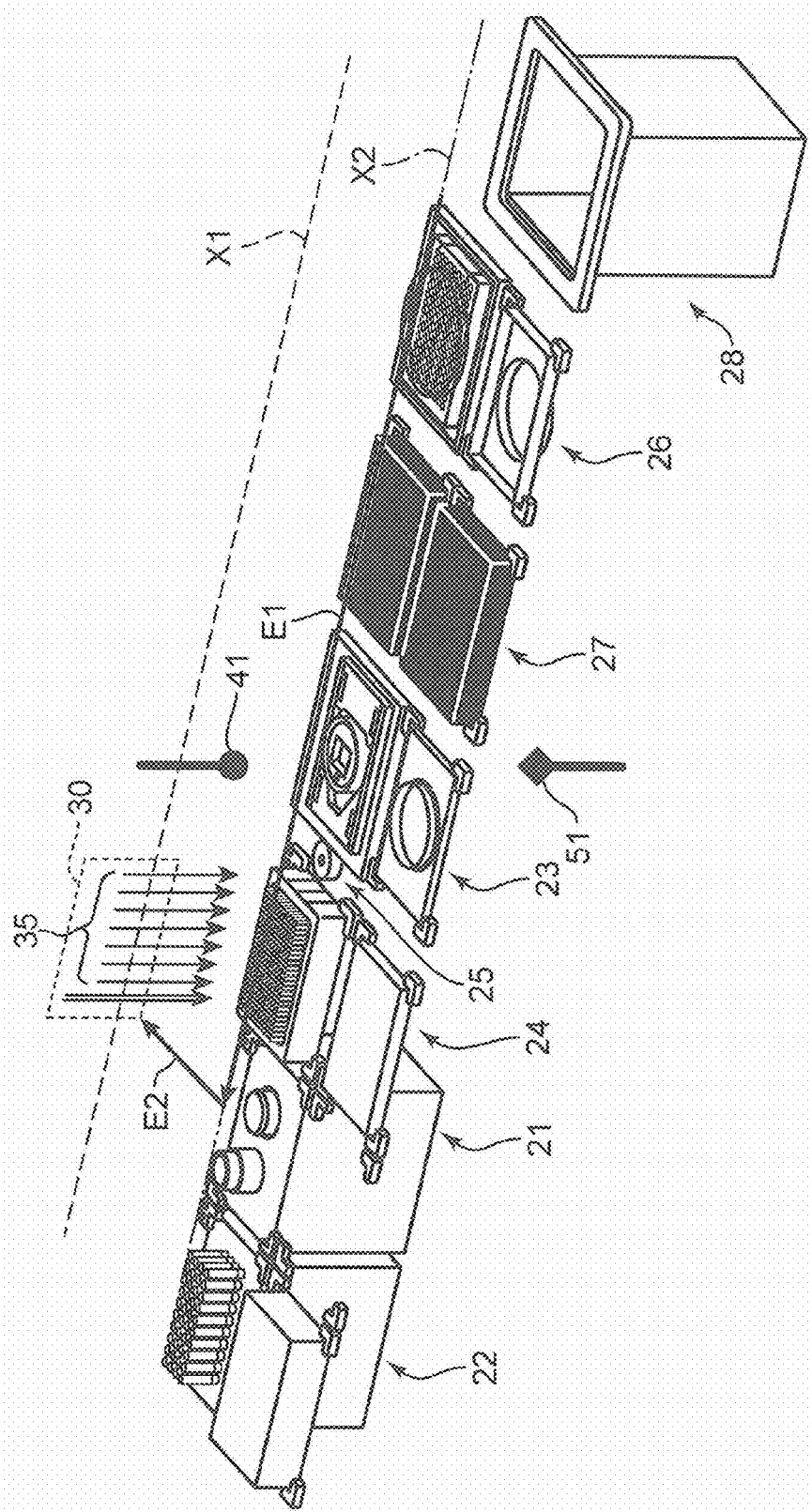
FIG. 18 is a perspective view showing a state of movement of a head section on the cell movement line.

Next, the cell movement operation will be described with reference to FIGS. 18 to 26 and 29. FIG. 18 is a diagram showing a movement state of the head unit 30 after the discarding process of the dispensing tip 80 in "control 4" described above. The shaft control section 152 controls the head unit driving device 161, as indicated by an arrow E1, to move the head unit 30 rightward on the path X2 from the tip discarding section 28 to the tip stocking section 24. Subsequently, the shaft control section 152 moves the head unit 30 in the rear direction from the path X2 toward the path X1 and causes the head unit 30 to stand by above the group of cylinder tips 70.

Figure 19:
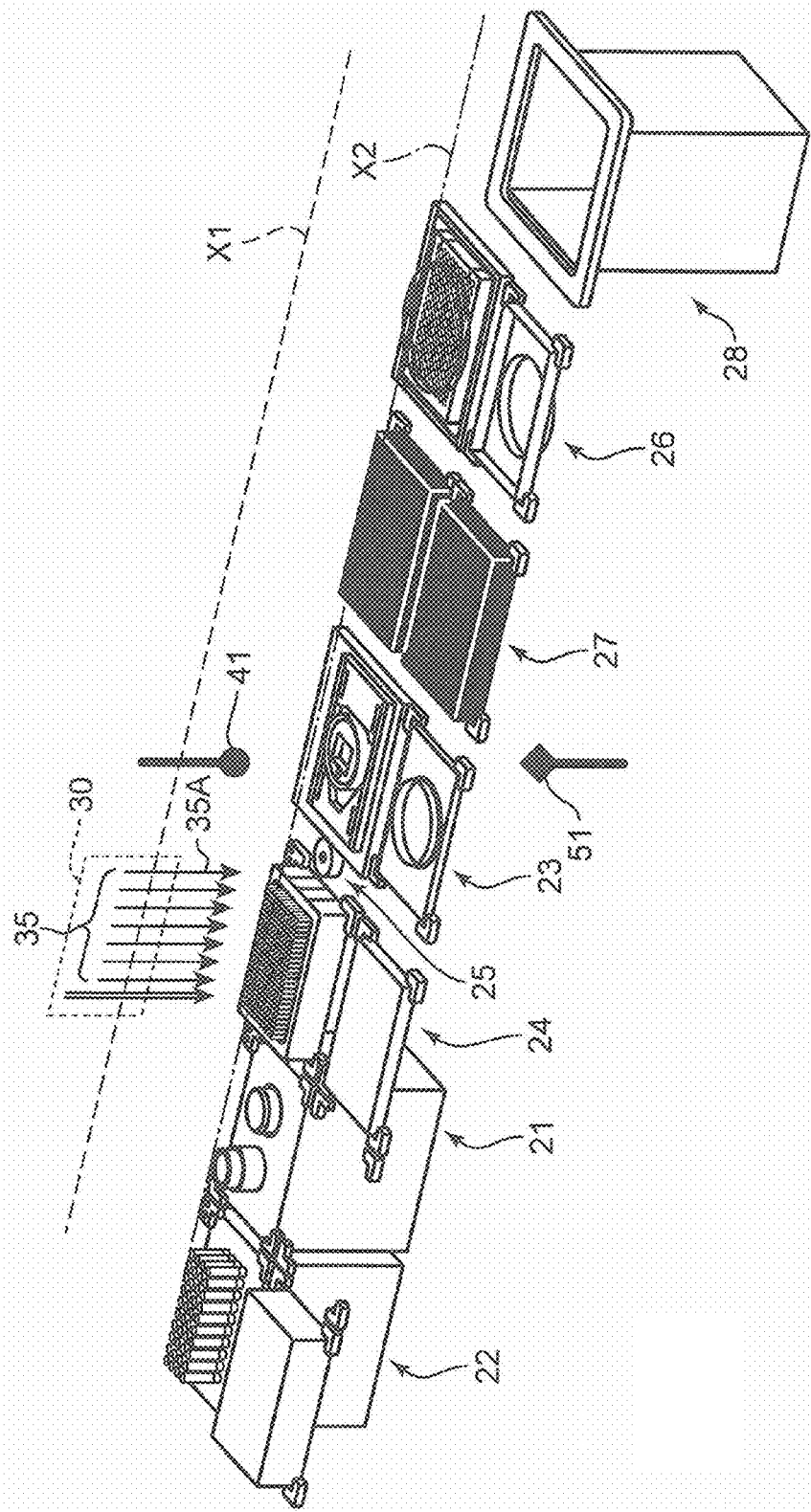
FIG. 19 is a perspective view showing a state of movement of a head section on the cell movement line.

Next, imaging of the dish 60 (the well plate 61) by the camera 51 is executed. FIG. 19 shows a state where the imaging is being performed. The imaging is a process for confirming at which position of the well plate 61 a cellular aggregate satisfying prescribed conditions (size, shape, and the like) exists (by which recessed section 61C the cellular aggregate is carried). Moreover, when a position of a cellular aggregate satisfying the prescribed conditions has been specified in the inspection step of "control 4" described earlier, the imaging operation at this point can be omitted.

Figure 20:
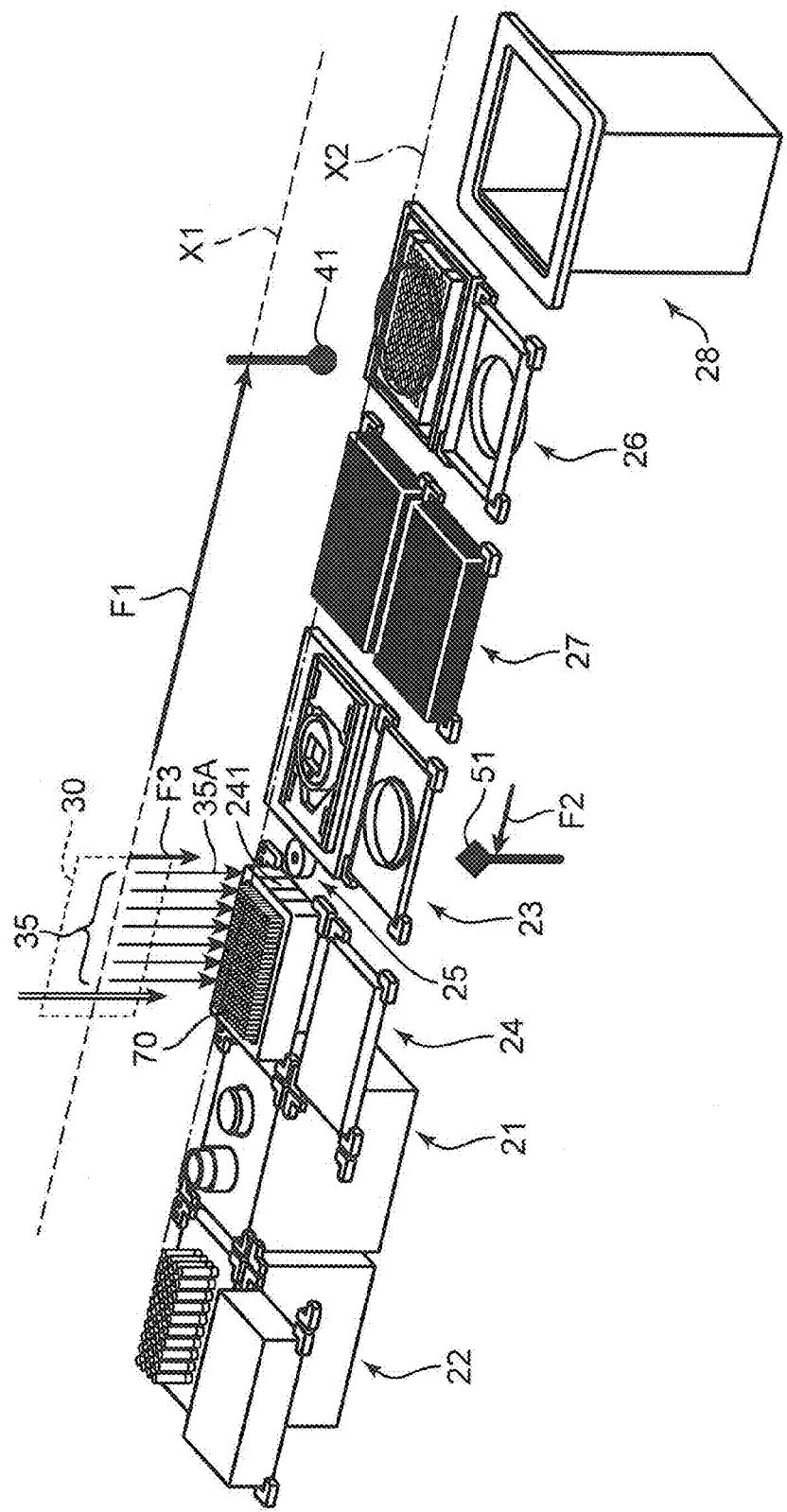
FIG. 20 is a perspective view showing a state of movement of a head section on the cell movement line.

FIG. 20 is a diagram showing a state where "control 5" described above is being executed. The head unit 30 is stopped above the holding box 241. At this point, the head unit 30 is stopped in a state where a rightmost rod section 35A among the plurality of rod sections 35 provided in the head section 32 is positioned with respect to one cylinder tip 70 determined in advance. An arrangement pitch of the cylinder tips 70 in the holder member 242 is set to an arrangement conforming to an arrangement pitch of the rod sections 35 and, when positioning of the rod section 35A and the one cylinder tip 70 is performed, a state is created where the other rod sections 35 are also positioned with respect to respectively opposing cylinder tips 70. Meanwhile, the illuminator 41 is moved rightward as indicated by an arrow F1 and stands by above the cell transferring section 26. In addition, the camera 51 is slightly moved leftward as indicated by an arrow F2 and stands by directly below the tip imaging section 25 in order to capture a recognition image of the cylinder tip 70.

Subsequently, the shaft control section 152 controls the head driving device 162 to collectively lower all of the rod sections 35 of the head section 32 as indicated by an arrow F3. Due to this operation, cylinder tips 70 are respectively attached to the rod sections 35. This attachment operation is as already described with reference to FIG. 10A. Obviously, instead of collectively lowering the rod sections 35, the rod sections 35 may be attached with the cylinder tip 70 one by one starting from the rightmost rod section 35A.

Figure 21:
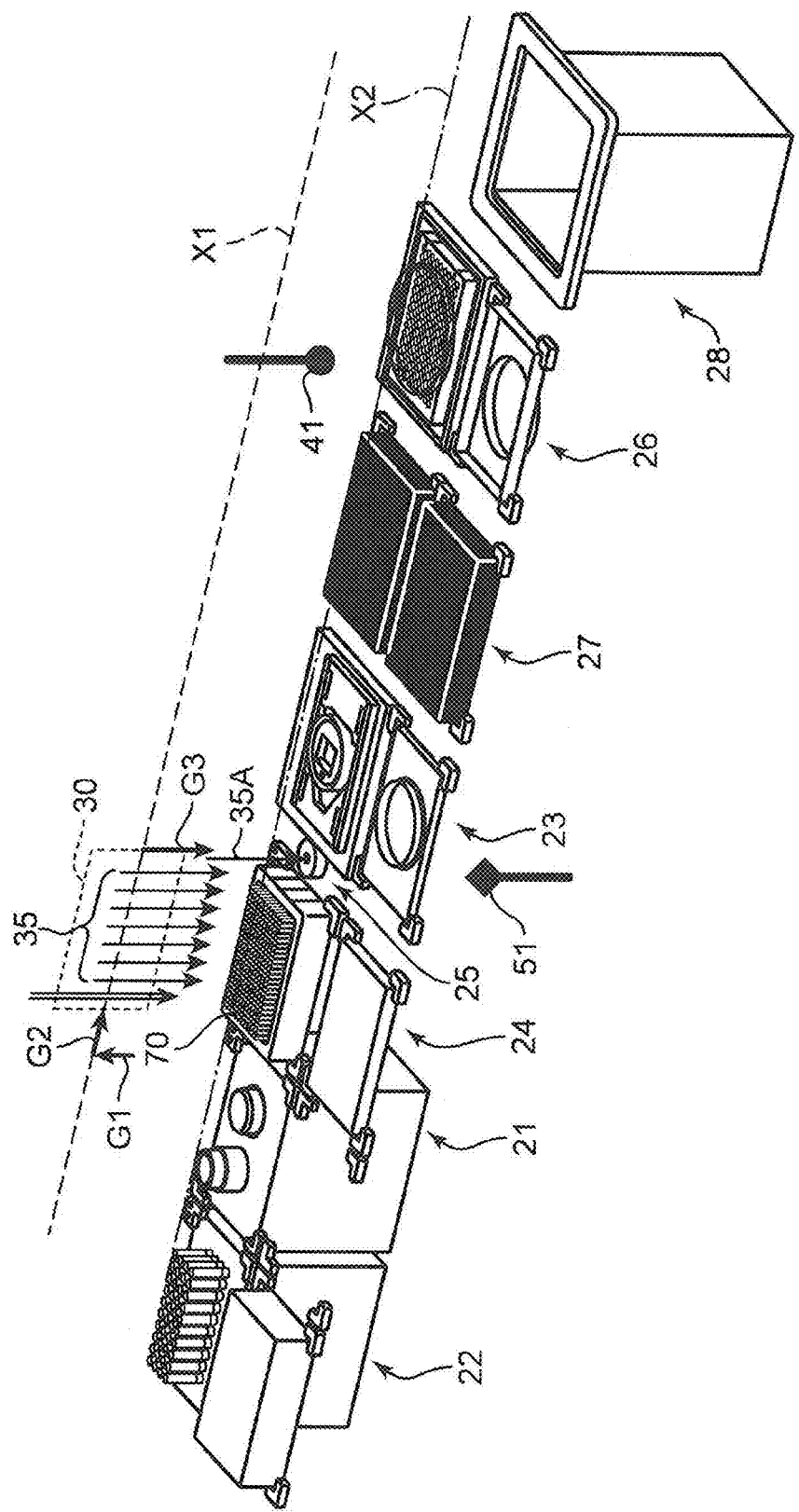
FIG. 21 is a perspective view showing a state of movement of a head section on the cell movement line.

FIG. 21 shows a state where imaging of the cylinder tip 70 attached to the rod section 35 is being performed at the tip imaging section 25. In this case, an attachment state of each cylinder tip 70 to the rod section 35 is detected and an XYZ coordinate position of the suction port 71T of the cylinder tip 70 (a correction value with respect to the XYZ coordinates of a distal end of the rod 351) is determined by the position correcting section 156. The shaft control section 152 first collectively raises the rod sections 35 respectively attached with the cylinder tips 70 from the state shown in FIG. 20 as indicated by an arrow G1. Subsequently, the shaft control section 152 moves the head unit 30 slightly rightward as indicated by an arrow G2 and stops the head unit 30 at a position where the rightmost rod section 35A opposes the tip imaging section 25. In addition, the camera control section 154 causes the camera 51 to capture an image of the cylinder tip 70. At this point, the lighting control section 153 turns on the vertical illuminator 52 in order to illuminate the cylinder tip 70.

Due to the imaging operation described above, the XYZ coordinate position of the suction port 71T of the cylinder tip 70 is determined. The Z coordinate position is determined from focal position information on the suction port 71T. Specifically, after lowering the cylinder tip 70 to a photography-enabled range, the rod section 35A is lowered in constant increments such as 10 μm increments (an arrow G3) and an image of the cylinder tip 70 is captured after each increment by the camera 51. At this point, a state exists where the plunger main body section 722 is deeply inserted into the syringe main body section 712 so that the distal end section 724 (FIG. 8) of the plunger 72 and the suction port 71T are flush with each other. This state at the start of suction of a cellular aggregate and, depending on an insertion state of the plunger main body section 722, a displacement of the suction port 71T may occur. Among the plurality of images obtained by the imaging, an image with a highest contrast is selected as a focused image and the Z coordinate position of the suction port 71T is determined from focal position information at the time of obtaining the focused image. In addition, due to image processing on the focused image, an XY coordinate position of the suction port 71T is obtained. As described earlier, a correction value representing a displacement with respect to the distal end of the rod 351 is derived from a difference between the XYZ coordinate position and a reference position determined in advance, and the correction value is stored in a storage section (not shown) in association with an identification code of the rod section 35A. Next, the shaft control section 152 slightly moves the head unit 30 rightward and causes the cylinder tip 70 attached to a rod section adjacent to the left side of the rod section 35A to oppose the tip imaging section 25. Subsequently, an imaging operation and a correction value deriving operation similar to those described above are performed with respect to the cylinder tip 70. Thereafter, similar operations are performed with respect to the remaining cylinder tips 70.

Figure 22:
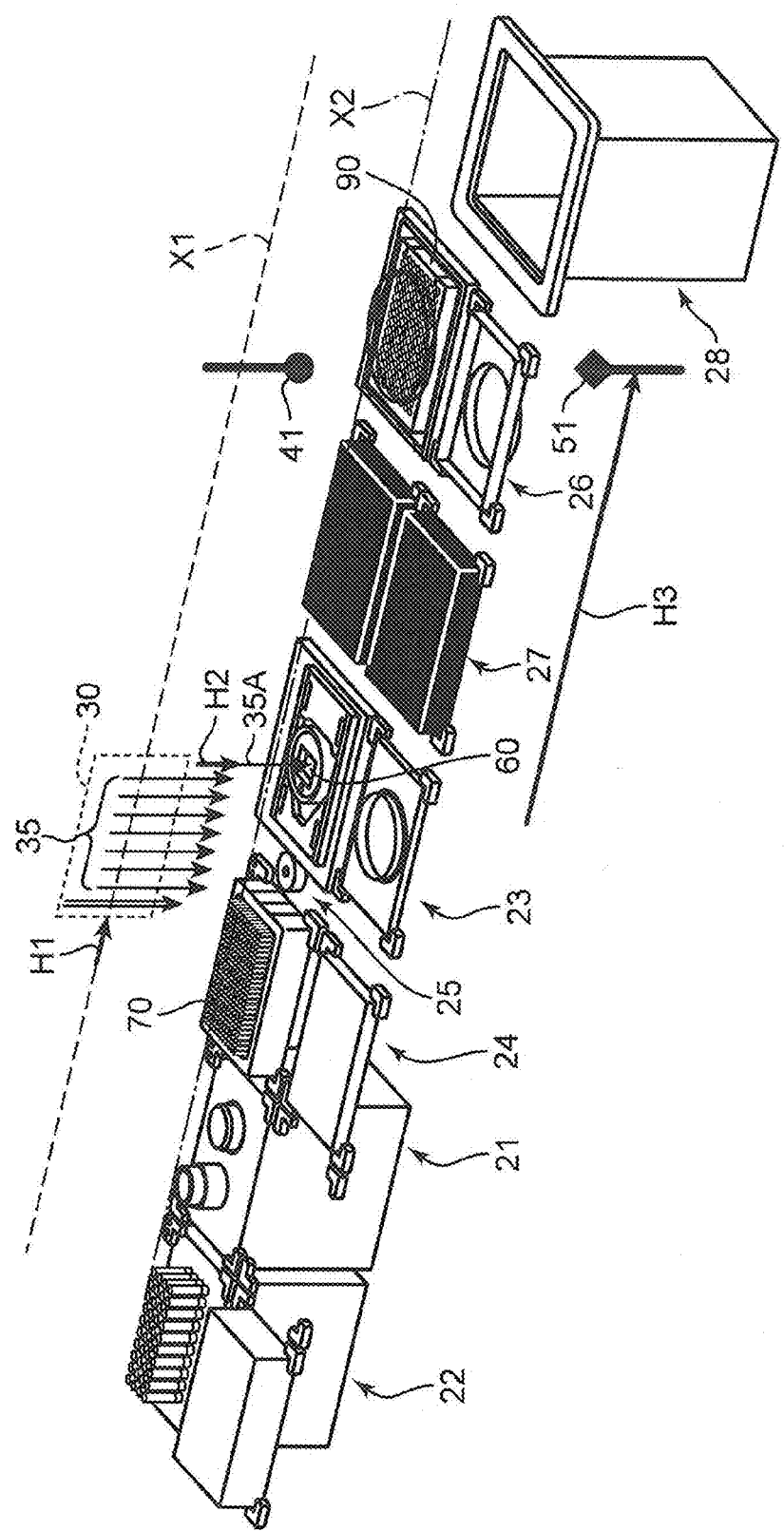
FIG. 22 is a perspective view showing a state of movement of a head section on the cell movement line.

FIG. 22 is a diagram showing a state where "control 6" described above is being executed. Suction of a cellular aggregate into the cylinder tip 70 is performed for each rod section 35. As indicated by an arrow H1, from the state shown in FIG. 21, the shaft control section 152 moves the head unit 30 from the tip imaging section 25 to above the cell selecting section 23 and stops the head unit 30 at a position where the rightmost rod section 35A opposes a prescribed position of the dish 60. The prescribed position is a position above the recessed section 61C of the well plate 61 which accommodates a cellular aggregate that is a suction target and which has been obtained based on the imaging of the dish 60 in FIG. 17 or 19 and on subsequent image processing.

Subsequently, as indicated by an arrow H2, the shaft control section 152 lowers the rod section 35A toward the dish 60. In addition, according to the method described with reference to FIGS. 9A to 9D, the cellular aggregate that is a suction target is suctioned into the cylinder tip 70 together with a cell culture solution. Subsequently, the rod section 35A is raised. Thereafter, the remaining rod sections 35 are positioned one by one with respect to a desired recessed section 61C and the lowering, suction, and raising operations described above are sequentially performed. During these operations, as indicated by an arrow H3, the shaft control section 152 controls the imaging unit driving device 164 to move the camera 51 rightward and causes the camera 51 to stand by directly below the cell transferring section 26. At this point, when a cellular aggregate is already being carried by the microplate 90, a sequence may be incorporated in which the camera control section 154 causes the camera 51 to capture an image of the microplate 90.

Figure 23:
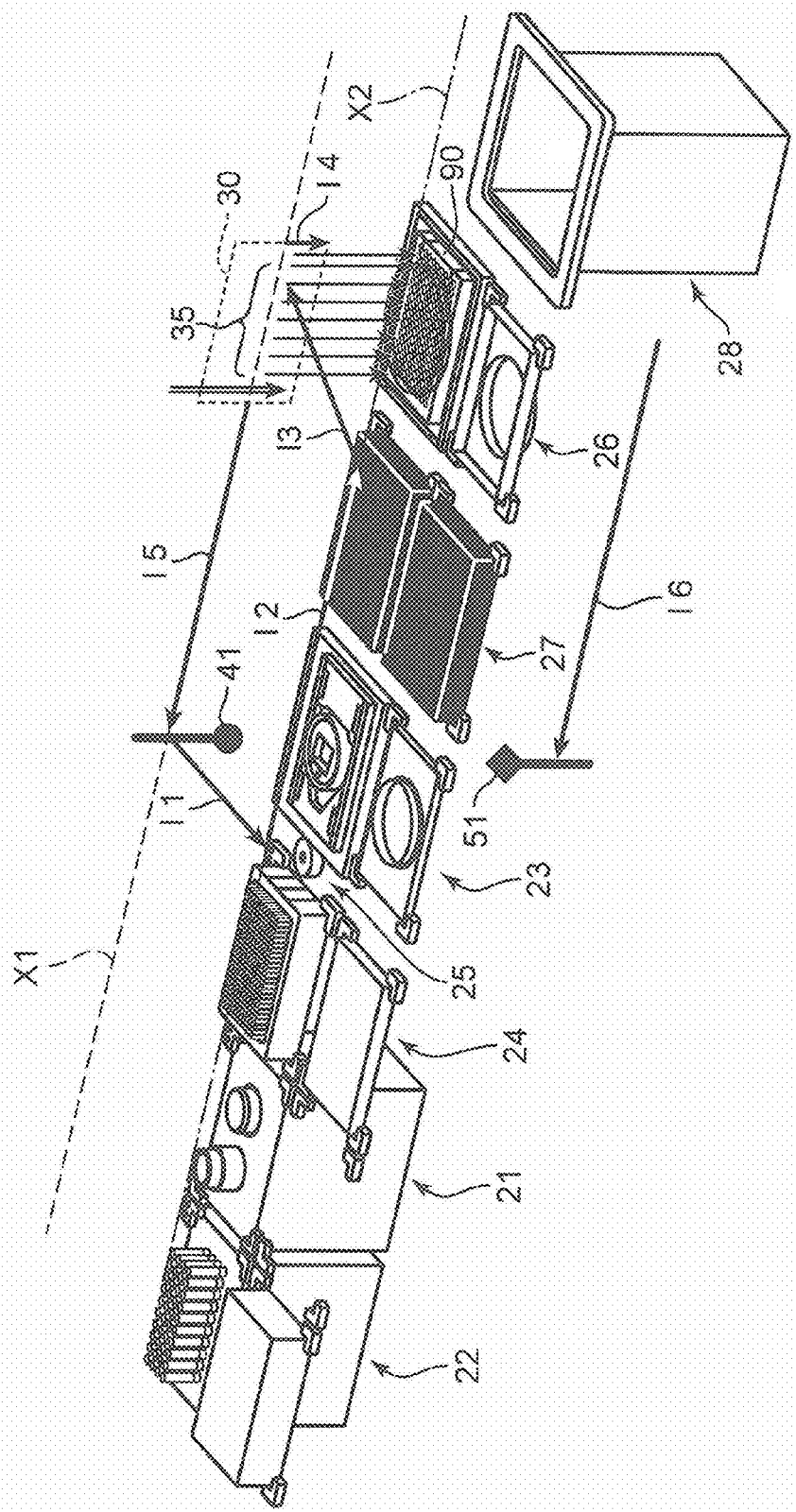
FIG. 23 is a perspective view showing a state of movement of a head section on the cell movement line.

FIG. 23 is a diagram showing a state where "control 7" described above is being executed. Upon executing "control 7", the shaft control section 251 moves the head unit 30 from above the cell selecting section 23 to above the cell transferring section 26 and, at the same time, moves the illuminator 41 from above the cell transferring section 26 to above the cell selecting section 23. Specifically, as indicated by arrows I1, I2, and I3, the shaft control section 152 temporarily moves the head unit 30 in a front direction from the path X1 toward the path X2 and, after moving the head unit 30 rightward on the path X2, moves the head unit 30 in a rear direction and stops the head unit 30 above the cell transferring section 26. In addition, as indicated by an arrow I5, the shaft control section 152 moves the illuminator 41 leftward along the path X1 and stops the illuminator 41 above the cell selecting section 23. As described above, since the head unit 30 and the illuminator 41 which are both arranged above the base 12 are moved so as to miss each other, interference does not occur between the head unit 30 and the illuminator 41 and a problem such as one of the head unit 30 and the illuminator 41 having to wait for the other to move does not occur.

Subsequently, the shaft control section 152 controls the head driving device 162 to collectively lower the rod sections 35 of the head section 32 toward the microplate 90 (an arrow I4). Next, according to the method described with reference to FIG. 9E, the cellular aggregates in the respective cylinder tips 70 are collectively discharged to the microplate 90. Obviously, instead of collectively discharging the cellular aggregates, the cellular aggregates can be discharged from one cylinder tip 70 at a time.

Moreover, the shaft control section 152 also moves the camera 51 to directly below the cell selecting section 23 as indicated by an arrow 16 at a timing of moving the illuminator 41. Accordingly, while a discharge operation by the cylinder tip 70 is being executed at the cell transferring section 26, an image of the cellular aggregate accommodated in (remaining in) the cell selecting section 23 can be captured by the camera 51. As a result, a contribution to a further reduction in cycle time can be made.

Figure 24:
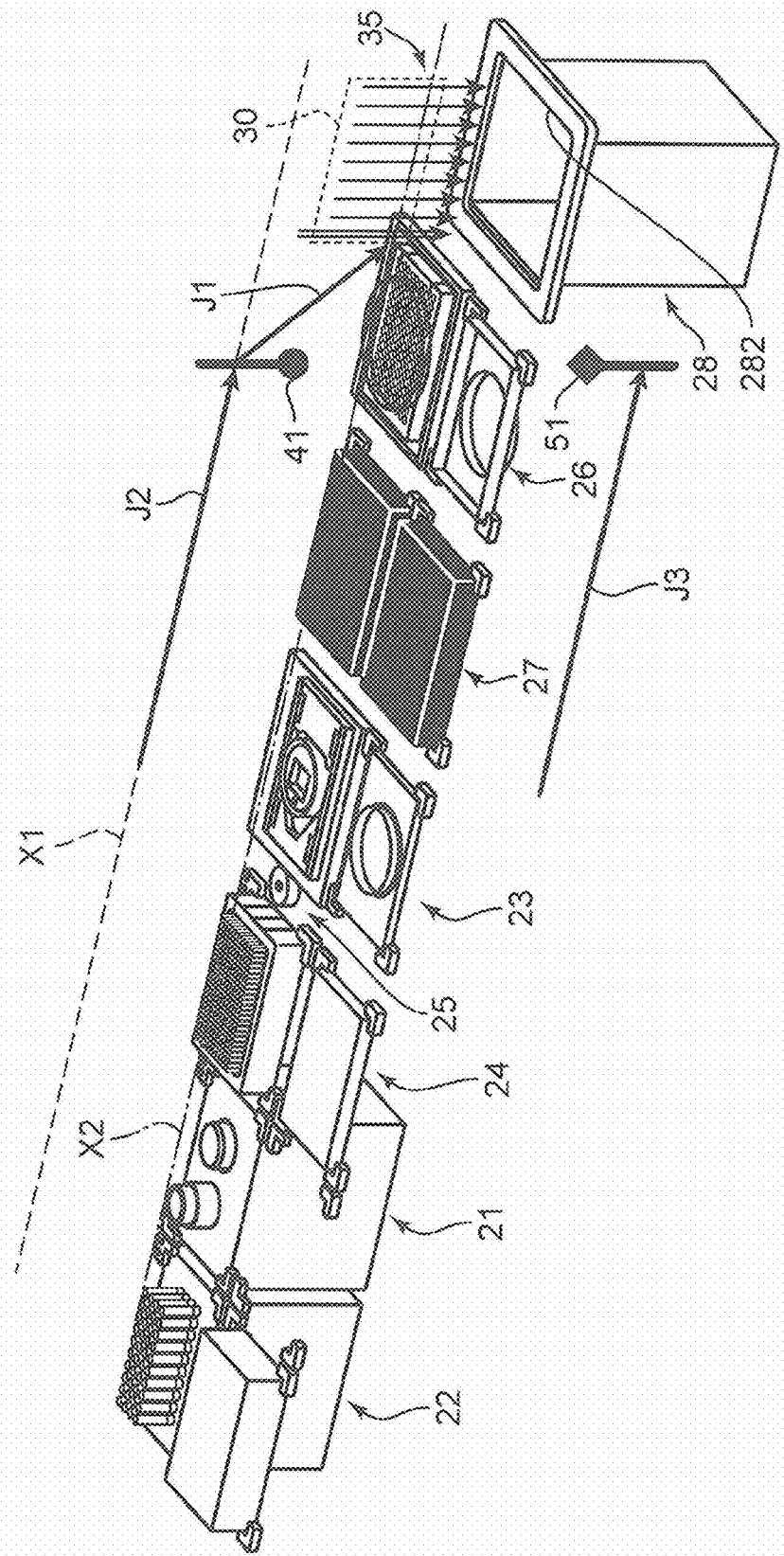
FIG. 24 is a perspective view showing a state of movement of a head section on the cell movement line.

FIG. 24 is a diagram showing a state where "control 8" described above is being executed. After raising the rod section 35 attached with the cylinder tip 70 from the state shown in FIG. 23, the shaft control section 152 moves the head unit 30 to above the tip discarding section 28 as indicated by an arrow J1. During the movement, the head unit 30 moves in the front direction from the path X1 toward the path X2 and subsequently moves rightward on the path X2 where the tip discarding section 28 is arranged. After stopping the head unit 30 above the tip discarding section 28, the shaft control section 152 controls the head driving device 162 to detach the cylinder tip 70 from the rod section 35 and discard the cylinder tip 70 into the collection box 281 according to the method described earlier with reference to FIG. 10B. Moreover, when chemicals or the like are not adhered to the cylinder tip 70 when discharging a cellular aggregate from the cylinder tip 70 to the microplate 90, discarding need not necessarily be executed after each discharge. Alternatively, the discarding of the cylinder tip 70 may be performed after confirming a carried state of a cellular aggregate by the microplate 90 through an image.

At a timing where discarding of the cylinder tip 70 described above is being performed, the shaft control section 152 controls the lighting unit driving device 163 to move the illuminator 41 from above the cell selecting section 23 to above the cell transferring section 26 as indicated by an arrow J2. In addition, the shaft control section 152 controls the imaging unit driving device 164 to move the camera 51 from below the cell selecting section 23 to below the cell transferring section 26 as indicated by an arrow J3.

Figure 25:
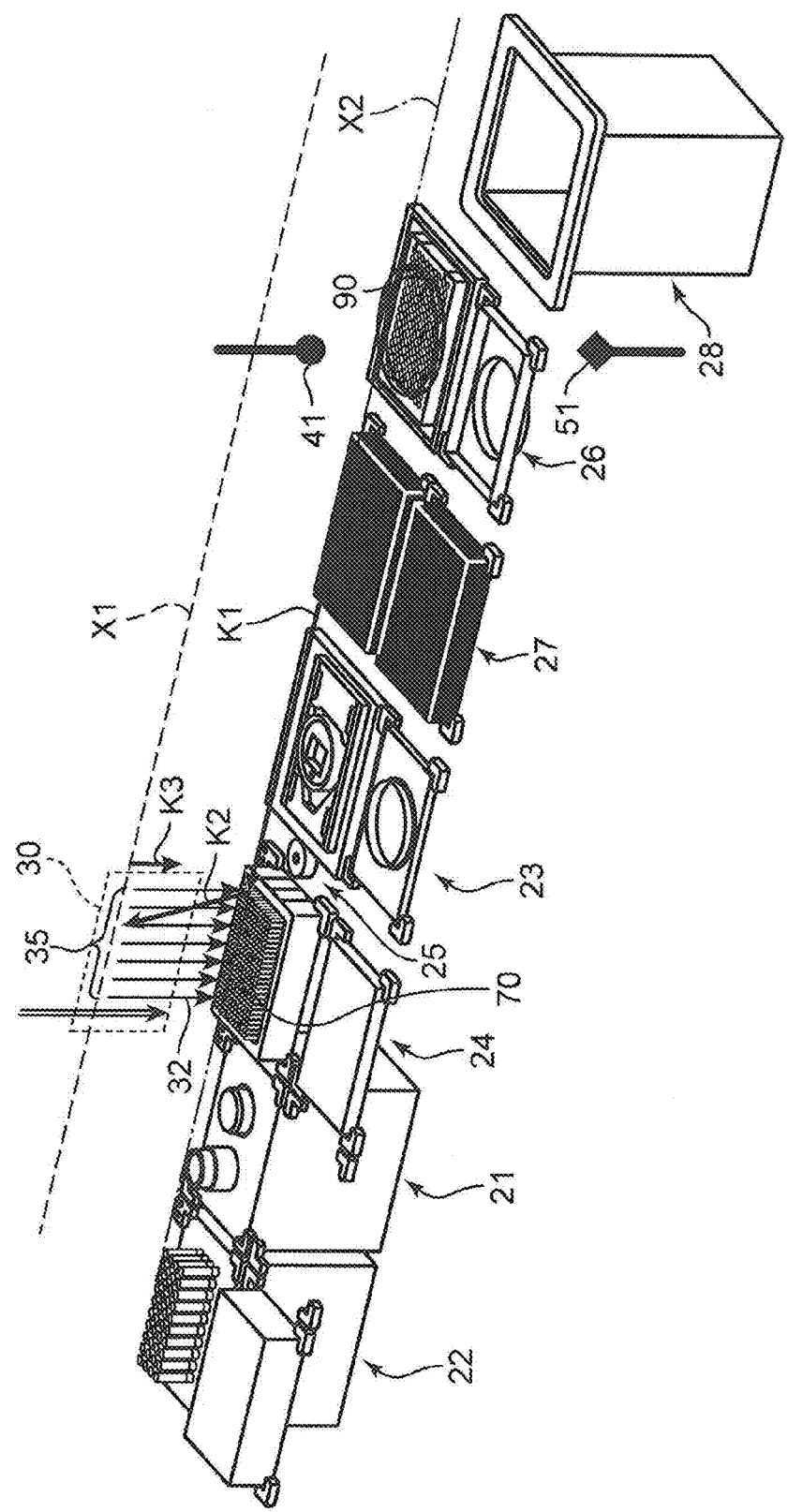
FIG. 25 is a perspective view showing a state of movement of a head section on the cell movement line.

FIG. 25 is a diagram showing a state where "control 5" described above for a cell movement operation of a next cycle is being executed. Subsequently, the shaft control section 152 moves the head unit 30 above the tip discarding section 28 leftward along the path X2 as indicated by an arrow K1, and further moves the head unit 30 in the rear direction from the path X2 toward the path X1 as indicated by an arrow K2 and causes the head unit 30 to stop above the cylinder tips 70 of the tip stocking section 24. In addition, the shaft control section 152 collectively lowers the rod sections 35 (an arrow K3) and attaches the cylinder tip 70 that is to perform a next suction operation to the rod section 35.

In parallel to the attachment operation of the cylinder tip 70 described above, imaging of the microplate 90 is performed in order to confirm whether or not a discharge of a cellular aggregate shown in FIG. 23 has been successful. Under control of the lighting control section 153 and the camera control section 154, the illuminator 41 emits transmissive illumination and the camera 51 captures an image of the microplate 90. The captured image is subjected to image processing by the image processing section 155 and displayed on the monitor 157. If a cellular aggregate is carried by the well 91 of the microplate 90 set as a discharge target, the discharge has succeeded. If a cellular aggregate is not carried by the well 91, the well 91 is once again set as a discharge target.

Figure 26:
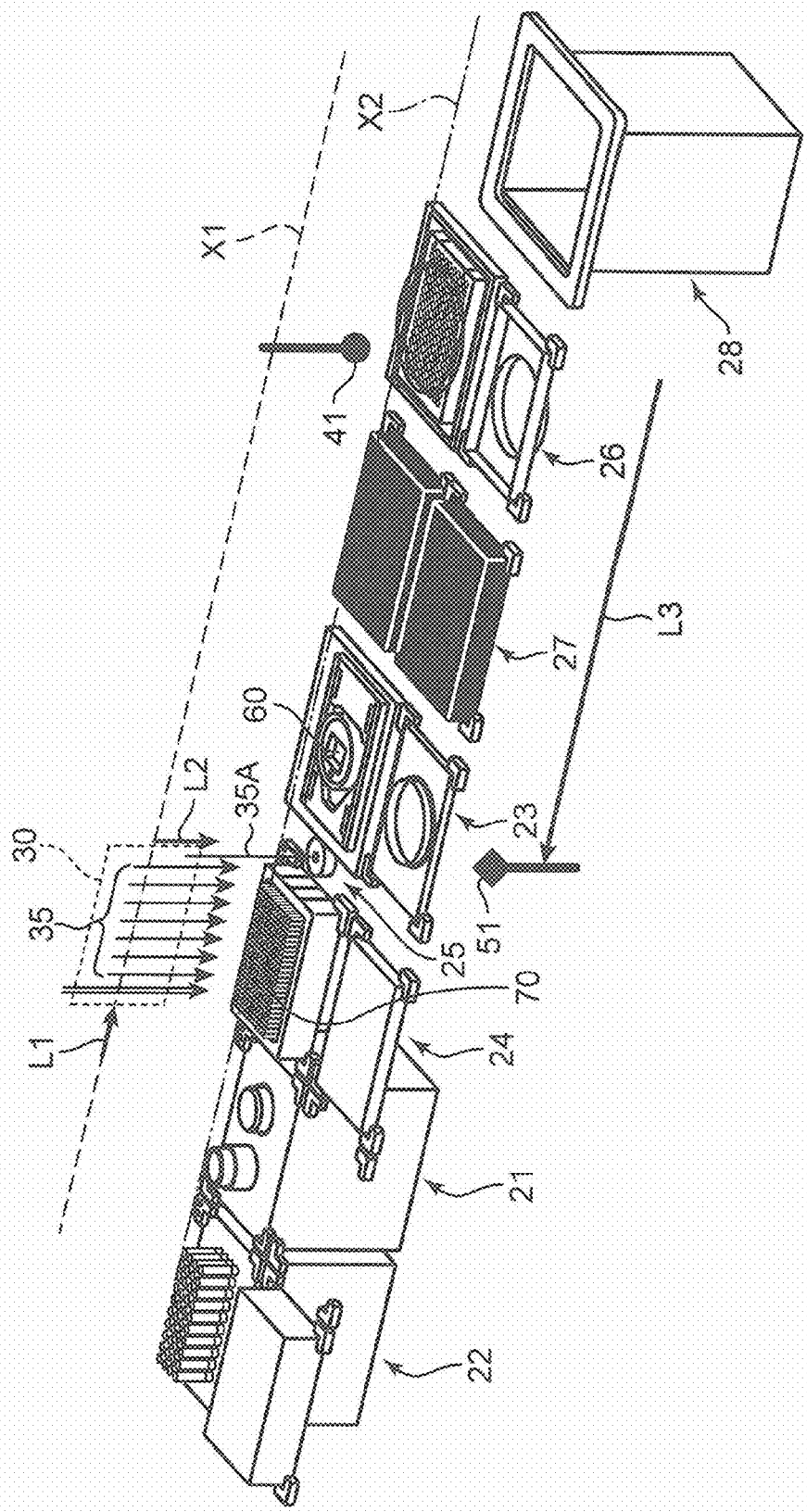
FIG. 26 is a perspective view showing a state of movement of a head section on the cell movement line.

FIG. 26 is a diagram showing a state where imaging of the cylinder tip 70 for a cell movement operation of a next cycle is being performed. The shaft control section 152 moves the head unit 30 rightward and positions the head unit 30 in the tip imaging section 25 as indicated by an arrow L1. In addition, the shaft control section 152 moves the camera 51 to directly below the tip imaging section 25 as indicated by an arrow L3. Subsequently, the shaft control section 152 lowers rod sections 35 to which new cylinder tips 70 have been attached one by one. This is the same operation as that described earlier with reference to FIG. 21. Accordingly, the XYZ coordinate position of the suction port 71T of the cylinder tip 70 is specified.

Thereafter, the operations described earlier with reference to FIGS. 22 to 26 are repeated. In other words, the main control section 151 repetitively executes "control 5" to "control 8" described above. The repetition is performed until cellular aggregates are carried by all of the wells 91 of the microplate 90. However, when the cylinder tip 70 in the holding box 241 becomes empty, the main control section 151 stops the device main body 10 and displays a message requesting that the cylinder tip 70 be replenished on the monitor 157. In addition, once it is confirmed that cellular aggregates are carried by all wells 91, the main control section 151 stops the device main body 10 and displays a message indicating that movement has been completed on the monitor 157.

Next, an additional operation when fluorescent photography is to be performed will be described with reference to FIGS. 27 to 29. FIGS. 27 and 28 are diagrams showing a state where "control 9" described above is being executed. In the drawings, the second nozzle 37 and the suction disk head 38 are additionally depicted in the head unit 30. The shaft control section 152 moves the head unit 30 to above the black cover mounting section 27, controls the head driving device 162 to lower the suction disk head 38 toward the first black cover 271. Once the suction disk head 38 comes into contact with an upper surface of the first black cover 271, the shaft control section 152 generates a suction force in the second nozzle 37 and causes the suction disk head 38 to adsorb the first black cover 271.

Subsequently, the shaft control section 152 raises the suction disk head 38 as indicated by an arrow M1 and then moves the head unit 30 rightward as indicated by an arrow M2. The shaft control section 152 stops the head unit 30 above the cell transferring section 26 and lowers the suction disk head 38 as indicated by an arrow M3. Accordingly, as shown in FIG. 28, a state is created where the microplate 90 is covered by the first black cover 271. Subsequently, the shaft control section 152 stops the suction force in the second nozzle 37 and releases the adsorption of the first black cover 271 by the suction disk head 38. In this state, the camera control section 154 causes the camera 51 to execute fluorescent observation of the cellular aggregate carried by the microplate 90. In doing so, a fluorescent illumination (not shown) mounted to the imaging unit 50 is turned on. After the observation, the first black cover 271 is returned to the black cover mounting section 27 in a reverse procedure to that described above.

The fluorescent observation operation can be successively executed after, for example, imaging of a cellular aggregate under the transmissive illumination shown in FIG. 25. While an example in which the microplate 90 is covered by the first black cover 271 has been shown above, a routine for covering the dish 60 with the second black cover 272 may be added.

With the moving device 1 according to the present embodiment described above, a series of operations from attachment of the cylinder tip 70 to the rod section 35, suction of a cellular aggregate from the dish 60 by the cylinder tip 70, discharge of the cellular aggregate to the microplate 90, to discarding of the cylinder tip 70 to the tip discarding section 28 can be automated under the control of the control section 15. Therefore, movement operational efficiency of a cellular aggregate can be increased significantly.

In addition, in the series of operations described above, the head unit 30 moves on the path X1 or the path X2 in one direction from left to right, and the tip stocking section 24, the cell selecting section 23, the cell transferring section 26, and the tip discarding section 28 are assembled to the base 12 on such a movement path in this order from left to right. This represents a layout capable of minimizing an amount of movement of the head unit 30 through the series of operations described above and, as a result, cycle time can be reduced.

Figure 30:
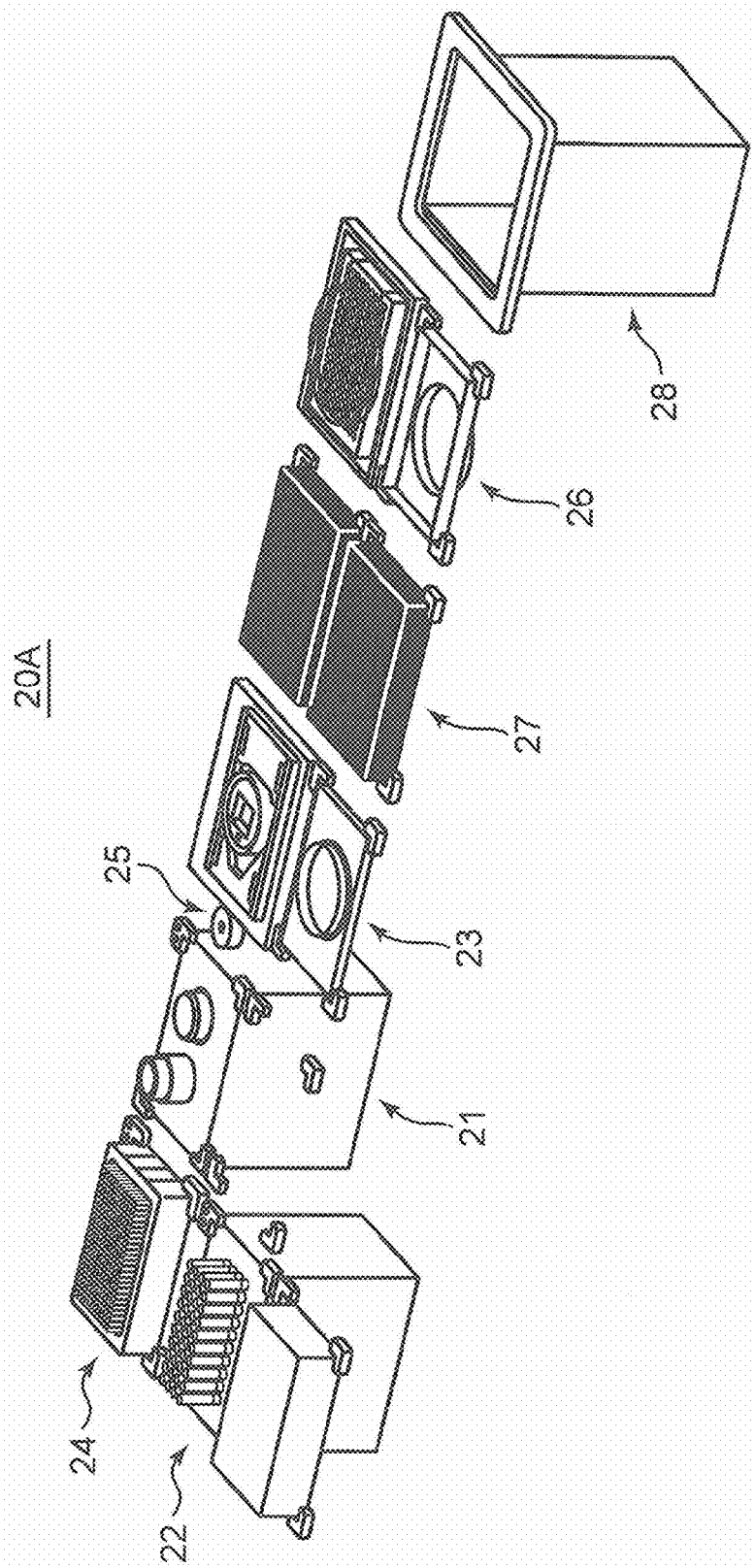
FIG. 30 is a perspective view showing a modification of a cell movement line.
Figure 31:
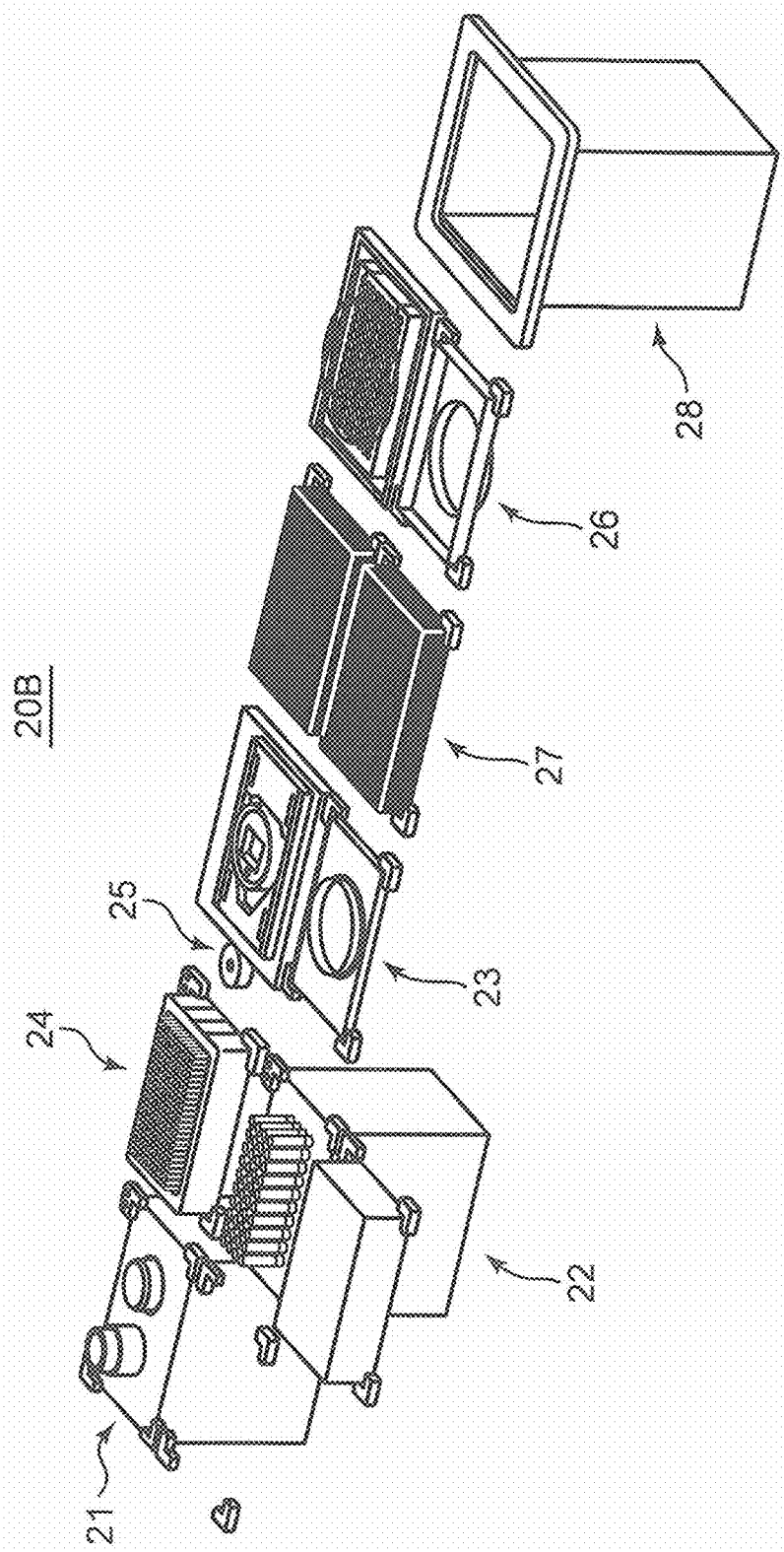
FIG. 31 is a perspective view showing a modification of a cell movement line.
Figure 32:
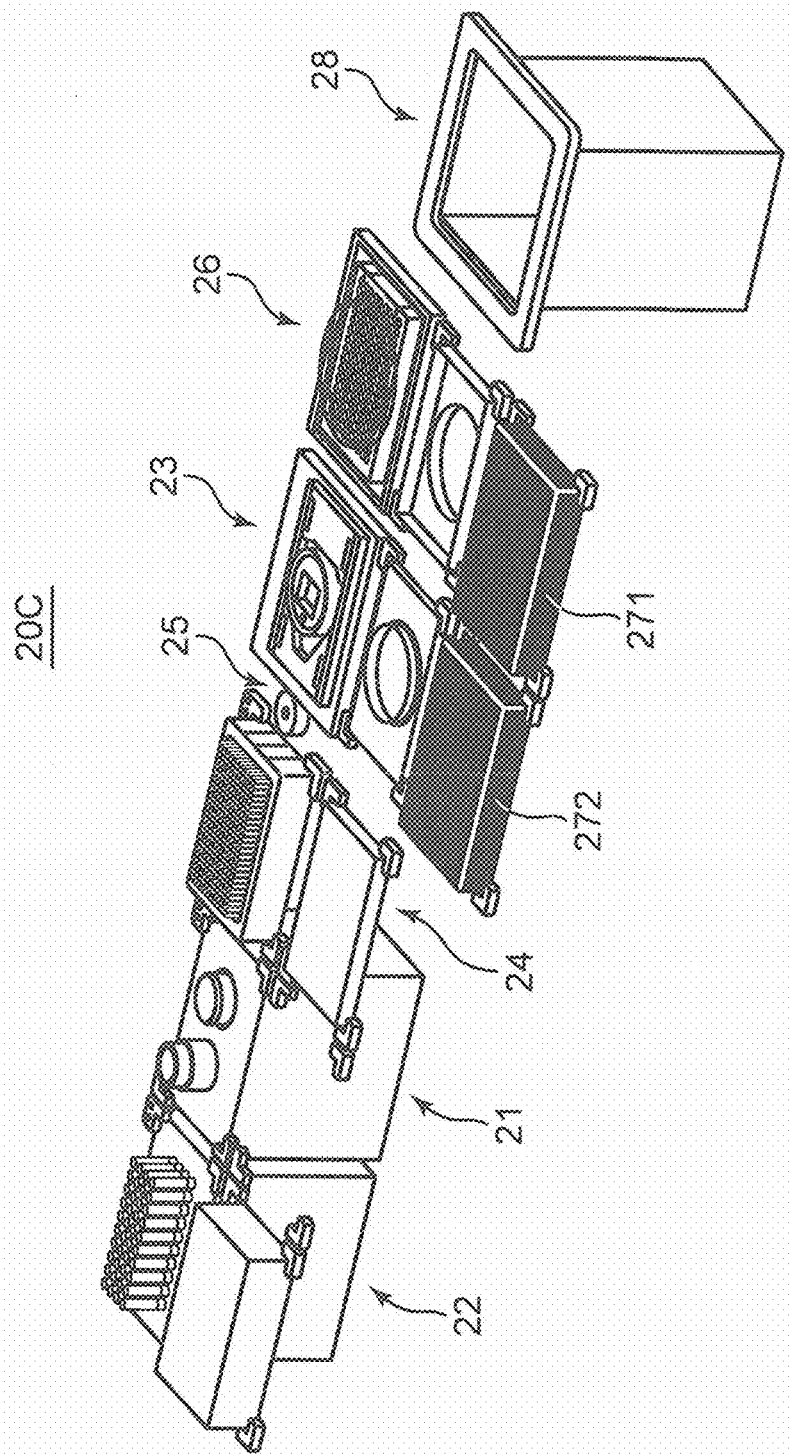
FIG. 32 is a perspective view showing a modification of a cell movement line.

Moreover, the layout of the cell movement line 20 described above is merely an example and the layout can be modified in various ways. FIGS. 30 to 32 show layouts of the cell movement line according to modifications. A cell movement line 20A shown in FIG. 30 differs from the cell movement line 20 shown in FIG. 4 in that the cell selecting section 23 is provided adjacent to the subject stocking section 21 and that the dispensing tip stocking section 22 and the tip stocking section 24 are arranged adjacent to the lift side of the subject stocking section 21. The layout of the cell movement line 20A is a layout suitable when a replacement frequency of the cylinder tip 70 is low. This layout has an advantage in that a problem of liquid dripping from the dispensing tip 80 to the tip stocking section 24 does not occur.

A cell movement line 20B shown in FIG. 31 differs from the cell movement line 20 shown in FIG. 4 in that the dispensing tip stocking section 22 is arranged parallel to the tip stocking section 24. In other words, in this layout, the dispensing tip stocking section 22 is also provided adjacent to the cell selecting section 23. The layout of the cell movement line 20B is a layout that is advantageous when the replacement frequency of the dispensing tip 80 is high.

A cell movement line 20C shown in FIG. 32 differs from the cell movement line 20 shown in FIG. 4 in that the first black cover 271 is arranged in front of the cell transferring section 26 and the second black cover 272 is arranged in front of the cell selecting section 23. With the layout of the cell movement line 20C, since a horizontal line width can be reduced by a width of the black cover mounting section 27, an advantage is gained in that a movement distance of the head unit 30 can be reduced.

The specific embodiment described above mainly includes an disclosure configured as described below.

A subject moving device according to an aspect of the present disclosure includes: a base; a head section which is provided with vertically movable rods and which moves along a prescribed movement path above the base; a first container section which has an open upper surface and which stores a subject of movement; a second container section which has an open upper surface and which receives the subject of movement; a tip stocking section which holds a plurality of tips in a state where the plurality of tips are attachable to the rods, the tips being attachable to and detachable from the rods and being configured to suction the subject of movement and discharge the suctioned subject of movement in accordance with vertical movements of the rods; a tip discarding section which collects the tips having finished the suction and the discharge of the subject of movement and having been detached from the rods; and a control section which controls the vertical movements of the rods and the movement operations of the head section, wherein the first container section, the second container section, the tip stocking section, and the tip discarding section are assembled to the base along a movement path of the head section, and control performed by the control section includes the following which are sequentially performed: first control for moving the head section to above the tip stocking section and attaching the tip to the rod; second control for moving the head section to above the first container section and suctioning the subject of movement stored in the first container section into the tip; third control for moving the head section to above the second container section and discharging the subject of movement inside the tip to the second container section; and fourth control for moving the head section to above the tip discarding section, and detaching the tip from the rod, and moreover discarding the tip to the tip discarding section.

According to the configuration described above, a series of operations from attachment of a tip to a rod, suction of a subject of movement from the first container section by the tip, discharge of the subject of movement to the second container section, to discarding of the tip to the tip discarding section can be automated under control of the control section. Therefore, movement operational efficiency of the subject of movement can be increased significantly.

In the moving device described above, desirably, the movement path is oriented in one direction, and the tip stocking section, the first container section, the second container section, and the tip discarding section are assembled to the base in this order from an upstream side toward a downstream side of the one direction.

According to this configuration, since a layout capable of minimizing an amount of movement of the head through the series of operations described above is realized, cycle time can be reduced.

In the moving device described above, desirably, a tip imaging device which images the tip attached to the rod after the first control is further provided, wherein the control section includes a position correcting section which obtains attachment position information on the tip, based on information obtained by the imaging operation.

According to this configuration, an attachment state of a tip to a rod can be discerned from a result of imaging by the tip imaging device, and when a displaced attachment has occurred, position correction data (attachment position information) can be obtained by the position correcting section. Therefore, positioning of the tip during the suction or the discharge can be performed at high accuracy.

In the moving device described above, desirably, the base, the first container section, and the second container section are made of translucent members, and the subject moving device further includes: a lighting section which has a light source, and which is arranged above the base so as to be movable at least between the first container section and the second container section, and moreover which illuminates the first container section or the second container section; and a subject observing device which has an imaging section, which is arranged below the base so as to be movable at least between the first container section and the second container section, and which acquires an image of the first container section or the second container section illuminated by the lighting section.

According to this configuration, an image of the first container section or the second container section can be captured by the subject observing device from below the base under illumination by the lighting section. Therefore, an observation image of the subject of movement in a state of being accommodated in the first container section or the second container section can be captured.

In this case, desirably, the moving device further includes a first driving mechanism which moves the head section and a second driving mechanism which moves the lighting section, the control section includes a drive control section which controls operations of the first driving mechanism and the second driving mechanism, and the drive control section arranges the head section above the first container section using the first driving mechanism and arranges the lighting section above the second container section using the second driving mechanism in the second control, and moves the head section from above the first container section to above the second container section using the first driving mechanism and moves the lighting section from above the second container section to above the first container section using the second driving mechanism in the third control.

According to this configuration, the head section and the lighting section which are both arranged above the base are moved so as to miss each other. Therefore, the first control to the fourth control described above can be executed without causing interference between the head section and the lighting section and without causing a problem where one of the head section and the lighting section must wait for the other to move.

In the moving device described above, desirably, a third driving mechanism which moves the subject observing device is further provided, wherein the drive control section also controls operations of the third driving mechanism, and the drive control section arranges the subject observing device below the second container section using the third driving mechanism in the second control and moves the subject observing device from below the second container section to below the first container section using the third driving mechanism in the third control.

According to this configuration, imaging can be performed by the subject observing device with respect to a subject of movement housed in the second container section while a suction operation by a tip is being executed at the first container section or with respect to a subject of movement housed in the first container section while a discharge operation by a tip is being executed at the second container section. As a result, by adopting this configuration, a contribution to a further reduction in cycle time can be made.

In the moving device described above, desirably, a black cover which is placed on the base and which is capable of covering and hiding the first container section or the second container section from above is further provided, wherein the head section further includes a suction disk head capable of adsorbing the black cover and releasing the adsorption.

According to this configuration, due to the head section provided with a suction disk head, the first container section or the second container section can be covered and hidden by the black cover when necessary. Therefore, for example, the moving device can be provided with a function that enables fluorescent observation and the like of a subject of movement to be executed easily.

In the moving device described above, desirably, the subject of movement is dispersed in a liquid, the moving device further includes: a third container section which has an opened upper surface and which stores a liquid containing the subject of movement; a nozzle which is provided in the head section and which is capable of generating a suction force and a discharge force; and a dispensing tip stocking section which holds a plurality of dispensing tips in a state where the dispensing tips are attachable to the nozzle, the dispensing tips being attachable to and detachable from the nozzle and being configured to suction the liquid containing the subject of movement when the suction force is imparted and to discharge the suctioned liquid when the discharge force is imparted, wherein the control section sequentially performs the following before the first control: control for moving the head section to above the dispensing tip stocking section and attaching the dispensing tip to the nozzle; control for moving the head section to above the third container section and suctioning a liquid containing the subject of movement stored in the third container section into the dispensing tip by a prescribed dispensing amount; control for moving the head section to above the first container section and discharging the liquid inside the dispensing tip to the first container section; and control for moving the head section to above the tip discarding section, and removing the dispensing tip from the nozzle, and moreover discarding the dispensing tip to the tip discarding section.

According to this configuration, a series of operations for dispensing a dispersion liquid of the subject of movement from the third container to the first container can be automated. In other words, a series of operations from attachment of a dispensing tip to a nozzle, suction of the dispersion liquid from the third container by the dispensing tip, discharge of the dispersion liquid to the second container section, to discarding of the dispensing tip to the tip discarding section can be automated under control of the control section.

In the moving device described above, desirably, the subject is a biological cell. In particular, the subject is desirably a biological cellular aggregate.

As described above, according to the present disclosure, in a moving device which moves a subject from one container to another container, the movement can be realized with good operational efficiency.

The invention claimed is:

1. A subject moving device comprising:
    a base;
    a head section which is provided with vertically movable rods and which moves along a prescribed movement path above the base;
    a first container section which has an open upper surface and which stores a subject of movement;
    a second container section which has an open upper surface and which receives the subject of movement;
    a tip stocking section which holds a plurality of tips in a state where the plurality of tips are attachable to the rods, the tips being attachable to and detachable from the rods and being configured to suction the subject of movement and discharge the suctioned subject of movement in accordance with vertical movements of the rods;
    a tip discarding section which collects the tips having finished the suction and the discharge of the subject of movement and having been detached from the rods;
    and a control section which controls the vertical movements of the rods and the movement operations of the head section, wherein
    the first container section, the second container section, the tip stocking section, and the tip discarding section are assembled to the base along a movement path of the head section, and
    control performed by the control section being configured to sequentially perform:
    first control for moving the head section to above the tip stocking section and attaching the tip to the rod;
    second control for moving the head section to above the first container section and suctioning the subject of movement stored in the first container section into the tip;
    third control for moving the head section to above the second container section and discharging the subject of movement inside the tip to the second container section;
    and fourth control for moving the head section to above the tip discarding section, and detaching the tip from the rod, and moreover discarding the tip to the tip discarding section,
    wherein the base, the first container section, and the second container section are made of translucent members, and the subject moving device further comprises:
    a lighting section which has a light source, and which is arranged above the base so as to be movable at least between the first container section and the second container section, and moreover which illuminates the first container section or the second container section; and
    a subject observing device which has an imaging section, and which is arranged below the base so as to be movable at least between the first container section and the second container section, and moreover which acquires an image of the first container section or the second container section illuminated by the lighting section.

2. The subject moving device according to claim 1, wherein
    the movement path is oriented in one direction, and
    the tip stocking section, the first container section, the second container section, and the tip discarding section are assembled to the base in this order from an upstream side toward a downstream side of the one direction.

3. The subject moving device according to claim 1, further comprising
    a tip imaging device which images the tip attached to the rod after the first control, wherein
    the control section includes a position correcting section which obtains attachment position information on the tip, based on information obtained by the imaging operation.

4. The subject moving device according to claim 1, further comprising: a first driving mechanism which moves the head section; and
    a second driving mechanism which moves the lighting section, wherein the control section includes a drive control section which controls operations of the first driving mechanism and the second driving mechanism, and the drive control section
    arranges the head section above the first container section using the first driving mechanism and arranges the lighting section above the second container section using the second driving mechanism in the second control, and
    moves the head section from above the first container section to above the second container section using the first driving mechanism and moves the lighting section from above the second container section to above the first container section using the second driving mechanism in the third control.

5. The subject moving device according to claim 4, further comprising
a third driving mechanism which moves the subject observing device, wherein
the drive control section also controls operations of the third driving mechanism, and
the drive control section
arranges the subject observing device below the second container section using the third driving mechanism in the second control, and
moves the subject observing device from below the second container section to below the first container section using the third driving mechanism in the third control.

6. The subject moving device according to claim 3, further comprising
a black cover which is placed on the base and which is capable of covering and hiding the first container section or the second container section from above, wherein
the head section further includes a suction disk head capable of adsorbing the black cover and releasing the adsorption.

7. The subject moving device according to claim 1, wherein
the subject of movement is dispersed in a liquid,
the moving device further comprises:
a third container section which has an opened upper surface and which stores a liquid containing the subject of movement;
a nozzle which is provided in the head section and which is capable of generating a suction force and a discharge force; and
a dispensing tip stocking section which holds a plurality of dispensing tips in a state where the dispensing tips are attachable to the nozzle, the dispensing tips being attachable to and detachable from the nozzle and being configured to suction the liquid containing the subject of movement when the suction force is imparted and to discharge the suctioned liquid when the discharge force is imparted, wherein
the control section sequentially performs the following before the first control:
control for moving the head section to above the dispensing tip stocking section and attaching the dispensing tip to the nozzle;
control for moving the head section to above the third container section and suctioning a liquid containing the subject of movement stored in the third container section into the dispensing tip by a prescribed dispensing amount;
control for moving the head section to above the first container section and discharging the liquid inside the dispensing tip to the first container section; and
control for moving the head section to above the tip discarding section, and removing the dispensing tip from the nozzle, and moreover discarding the dispensing tip to the tip discarding section.

8. The subject moving device according to claim 1, wherein
the subject is a biological cell.

9. The subject moving device according to claim 8, wherein
the subject is a biological cellular aggregate.

* * * * *